(12) United States Patent
Hoos et al.

(10) Patent No.: US 11,504,169 B2
(45) Date of Patent: *Nov. 22, 2022

(54) SURGICAL DEPTH INSTRUMENT

(71) Applicant: EDGE SURGICAL, INC., Chicago, IL (US)

(72) Inventors: Kenneth Hoos, Chicago, IL (US); Robert F. Rioux, Ashland, MA (US)

(73) Assignee: EDGE SURGICAL, INC., Chicago, IL (US)

( * ) Notice: Subject to any disclaimer, the term of this patent is extended or adjusted under 35 U.S.C. 154(b) by 506 days.

This patent is subject to a terminal disclaimer.

(21) Appl. No.: 16/810,320

(22) Filed: Mar. 5, 2020

(65) Prior Publication Data

US 2020/0289171 A1    Sep. 17, 2020

Related U.S. Application Data

(60) Provisional application No. 62/937,526, filed on Nov. 19, 2019, provisional application No. 62/816,536, filed on Mar. 11, 2019.

(51) Int. Cl.
*A61B 17/70* (2006.01)
*A61B 90/00* (2016.01)
(Continued)

(52) U.S. Cl.
CPC ...... *A61B 17/7092* (2013.01); *A61B 17/1728* (2013.01); *A61B 17/58* (2013.01); *A61B 90/06* (2016.02); *A61B 90/36* (2016.02); *A61B 2090/036* (2016.02); *A61B 2090/062* (2016.02); *A61B 2090/0811* (2016.02); *A61B 2560/0431* (2013.01); *A61B 2562/02* (2013.01); *A61B 2562/0247* (2013.01); *A61B 2562/166* (2013.01)

(58) Field of Classification Search
CPC . A61B 17/7092; A61B 17/1728; A61B 17/58; A61B 90/06; A61B 2090/036; A61B 2090/062; A61B 2090/0811; A61B 2560/0431; A61B 2562/02; A61B 2562/0247; A61B 2562/166
See application file for complete search history.

(56) References Cited

U.S. PATENT DOCUMENTS 10,151,570 B2 * 12/2018 Jacobs ................. B23B 49/00
10,578,415 B2 * 3/2020 Rioux .................. G01B 3/205
(Continued)

FOREIGN PATENT DOCUMENTS

KR           101277765 B1    6/2013

OTHER PUBLICATIONS

International Search Report and Written Opinion issued in International Application No. PCT/US2020/021176, dated Jun. 29, 2020, 11 pages.

(Continued)

*Primary Examiner* — Jonathan T Kuo
(74) *Attorney, Agent, or Firm* — Brown Rudnick LLP

(57) ABSTRACT

A device configured to provide a faster and more accurate measurement of depths of holes for placement of bone screws and fastener for bone implant fixation procedures. The device includes a combination of a bone probe for physical examination of a hole drilled in a bone and a depth gauge member for determining a depth of the hole and providing digital measurement of the depth.

15 Claims, 29 Drawing Sheets

(51) Int. Cl.
    *A61B 17/17*     (2006.01)
    *A61B 17/58*     (2006.01)

(56) References Cited

U.S. PATENT DOCUMENTS

| | | | |
|---|---|---|---|
| 2018/0195849 A1* | 7/2018 | Jacobs | B23B 49/00 |
| 2018/0214234 A1 | 8/2018 | Henry et al. | |
| 2018/0214235 A1 | 8/2018 | Dell'Oca et al. | |
| 2018/0250020 A1 | 9/2018 | Carusillo | |
| 2019/0049227 A1* | 2/2019 | Rioux | A61B 17/17 |
| 2020/0289172 A1* | 9/2020 | Hoos | A61B 90/36 |

OTHER PUBLICATIONS

International Search Report and Written Opinion issued in International Application No. PCT/US2020/021172, dated Jun. 15, 2020. 12 pages.

* cited by examiner

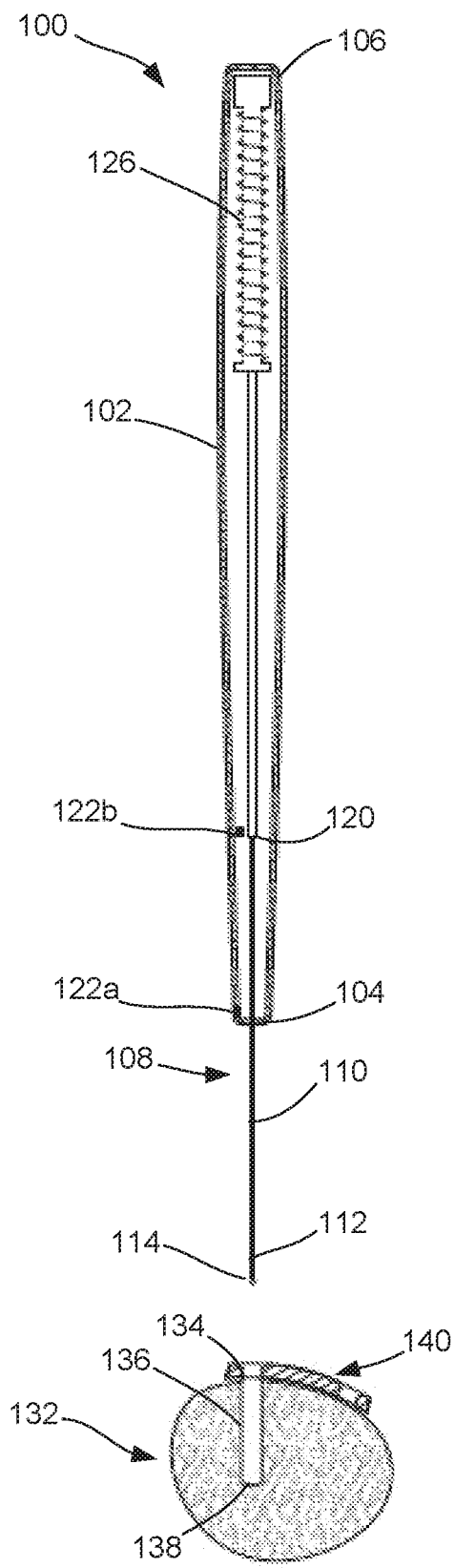
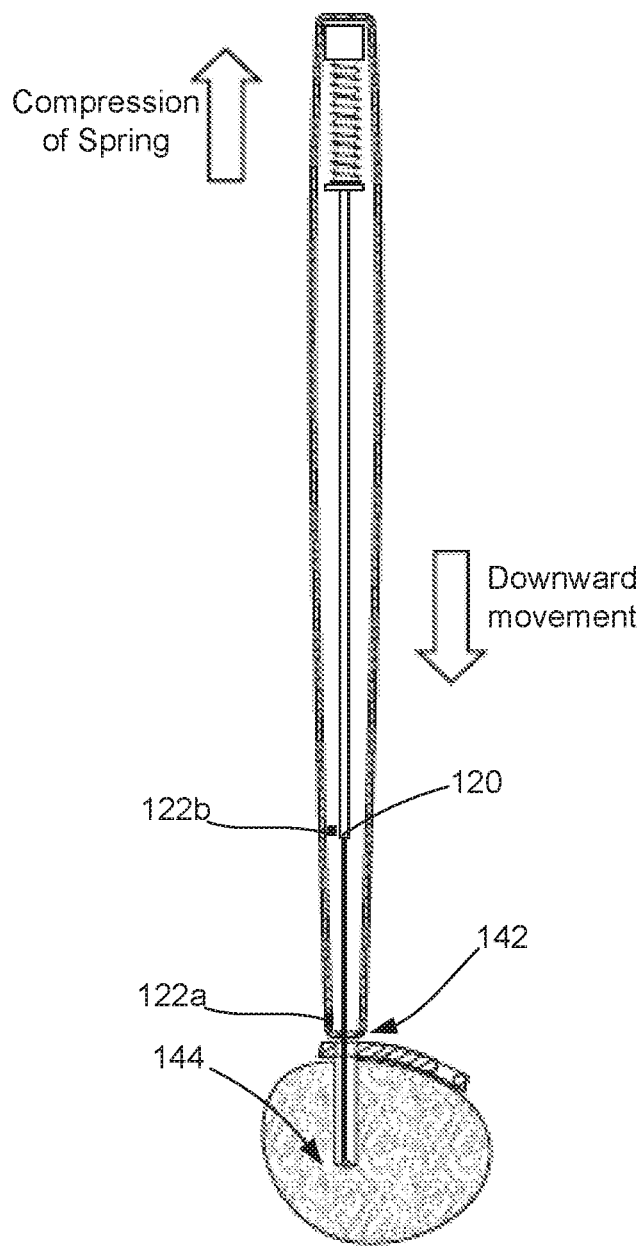
FIG. 10A
FIG. 10B

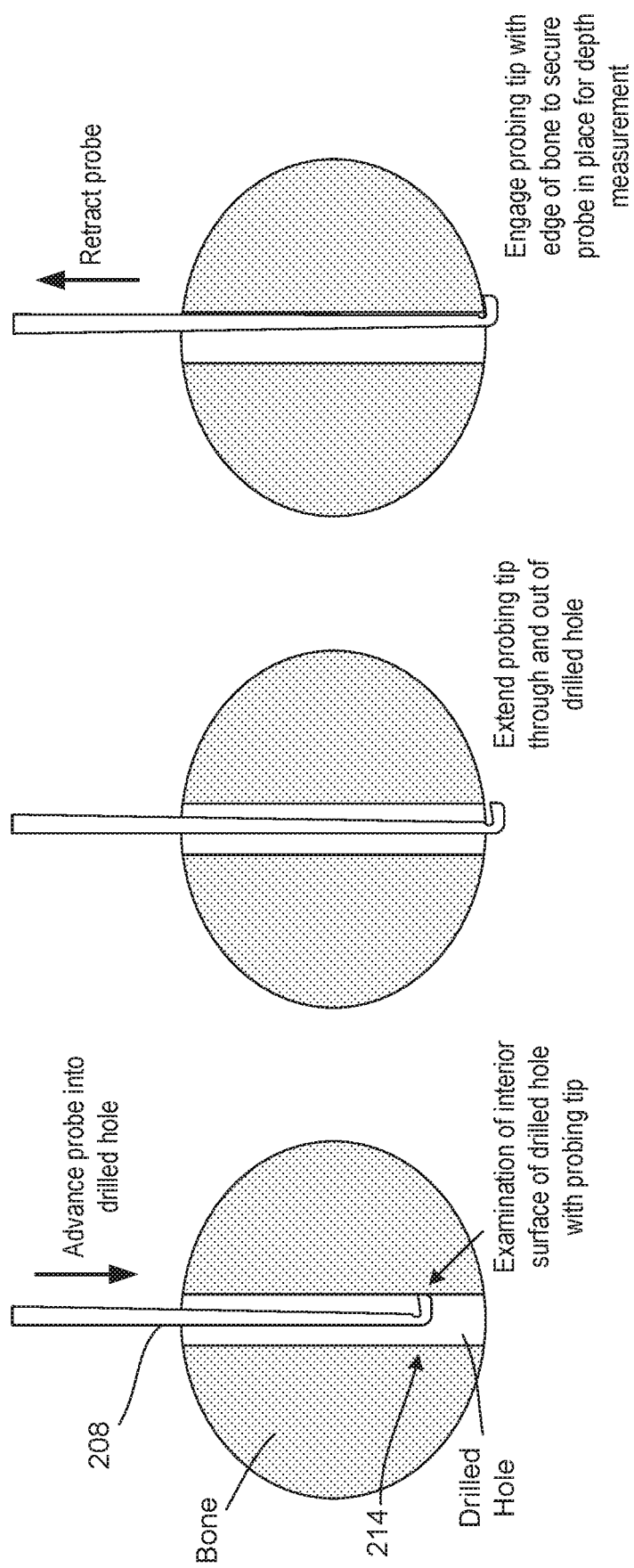

SURGICAL DEPTH INSTRUMENT

CROSS-REFERENCE TO RELATED APPLICATIONS

The application claims the benefit of, and priority to, U.S. Provisional Application No. 62/937,526, filed on Nov. 19, 2019 and U.S. Provisional Application No. 62/816,536, filed on Mar. 11, 2019, the contents of each are incorporated by reference herein in their entireties.

FIELD

The present disclosure relates generally to medical devices, and, more particularly, to a measuring instrument for use in a bone implant fixation procedure, the measuring instrument including a combination of a bone probe allowing for physical examination of a hole drilled in a bone and a depth gauge member for determining a depth of the hole and providing a digital measurement of the depth.

BACKGROUND

Orthopedics is a medical specialty concerned with the correction of deformities or functional impairments of the skeletal system, especially the extremities and the spine, and associated structures, such as muscles and ligaments. Some orthopedic surgical procedures require surgeons to secure a device to one or more bones of a patient. For example, in some procedures, the surgeon may span and secures one or more bones, or pieces of a single bone, using a bone plate and one or more fasteners, such as screws. Other bone-related surgical procedures, however, may not require a bone plate and may instead solely rely on the use of one or more screws (e.g., securing a transplanted tendon).

In such bone-related surgical procedures, before an implant or plate, or simply the screw itself, can be attached to bone, an opening is typically drilled into the bone to accommodate the screw. With a hole in place, the surgeon can more easily select a screw of the appropriate length. However, selecting a screw of appropriate length is critical. For example, if the selected screw is too long, the distal end of the screw may pass through the end of the drilled hole and cause damage to the bone and/or protrude entirely through the bone, which can have deleterious effects, such as damage to surrounding tissue and/or pain and discomfort, or more serious complications, for the patient. For example, in some instances, the bone may abut against soft tissues that may be harmed if the screw is too long and may result in irritation of or damage to the soft parts. Additionally, a screw that protrudes through the bone may be tactilely felt by the patient, may prevent soft tissues (e.g., tendons, ligaments, or muscles) from moving over the bone surface as intended, or may even pierce the skin, which can lead to serious infection and complications.

The selection of an appropriate length screw is particularly important in spinal fixation procedures, such as lumbar sacral fusion and the correction of spinal deformities such as scoliotic curves. As an example, a screw mounted in the pedicle portion of the human spine should not extend to a point where the screw contacts the spinal cord itself, an event that can cause irreparable nervous system damage including paralysis. Accordingly, the determination of a length of the hole is important for choosing the appropriate length screw.

During drilling, the surgeon is typically capable of recognizing the resistance on the drill in order to determine when the drill has penetrated through the bone. Because the simple act of drilling does not provide an exact measurement of the depth of the bone itself, a depth gauge is commonly employed for directly measuring the depth of the hole from the top, drilling side to the bottom, opposite side of the hole.

Currently, many designs are known and utilized for measuring the depth of a hole or bore in a portion of a bone. Generally speaking, these designs utilize a central probe member having a barb at a distal end, and a sleeve or channel member. The probe member is inserted into the pilot hole while the surgeon attempts to find the surface with the barb. More specifically, the probe member is inserted to a depth greater than the depth of the pilot hole so that the barb is beyond the opposite side, at which point the surgeon finds the surface by hooking the barb to the opposite side.

The probe member is received in the sleeve or channel member and may reciprocate relative thereto. The channel member has graduated markings along a portion of its length, typically in inches and/or millimeters. A marker is laterally secured to the probe member such that, as the probe member shifts relative to the channel member, the marker indicates the relative shift between the probe member and the channel member. Accordingly, once the probe member has been secured to the opposite side of the bone, the channel member is shifted relative to the probe member and toward the bone until the channel member abuts the surface of the bone. The depth gauge is then read by examining graduated markings indicated by the probe member marker.

A number of problems are experienced with this depth gauge. As an initial point, the components are typically made with surgical-grade stainless steel, and the graduated markings are embossed therein. Therefore, the brightness of the operating room lights on the highly reflective surface can make the markings difficult to read. The markings are commonly in small increments, such as millimeters, and surgeons often have trouble differentiating between the markings, or noting partial increments. Reading these gauges, then, often requires carefully holding the depth gauge as the reading is taken, and a surgeon's effort to closely examine the reading may result in a loss of securement or purchase of the barb on the bone, thus necessitating a re-measurement and a loss of time.

Furthermore, proper reading of the markings requires a surgeon's eyes to be properly aligned with the markings. That is, a proper view of the measurement requires the surgeon to view the gauge from a lateral point of view so that the view of the probe marker aligned with the graduated markings is proper not distorted by the surgeon's elevated, standing perspective. Therefore, it is often necessary for the surgeon to bend over while using these gauges to view an accurate reading. If the depth gauge is tilted in order to make the reading, the sleeve will shift relative to the probe, thus making the measurement inaccurate and possibly causing the barb to become unsecured, as described above. In addition, removal of the depth gauge often causes the measurement to be lost. As the bone is essentially clamped, by light pressure, between the distal end of the channel member and the distal barb of the probe member, it is often necessary to retract the channel member from the bone surface in order to extract the probe from the pilot hole.

SUMMARY

The present disclosure is a medical device for use in a bone implant fixation procedure. The device is configured to provide a faster and more accurate measure of depth. In particular, the device includes a combination of a bone probe allowing for physical examination of a hole drilled in a bone and a depth gauge member for determining a depth of the hole and providing a digital measurement of the depth. Accordingly, the device of the present disclosure is capable of digitally measuring the depth of an opening in a bone during the same surgical step that a surgeon probes and inspects the interior of the opening.

During a bone-related procedure involving placement of a screw, or other fastener, it may be desirable to determine whether drilling of the hole resulted in any cracks or openings, either along an interior side wall of the hole or at the base of the hole. Ensuring the integrity of the drilled hole is important because unintended cracks, openings, or irregularities can increase the risk that the screw will either not securely attach itself within the hole or may result in chipping or fragmenting of bone during fastening of the screw within the hole. It is generally not possible for a surgeon to visual examine the integrity of the drilled hole due to a limited field of view within the hole (drilled holes can be relatively small in width, such as 5 mm or less in some instances).

The device of the present disclosure includes a bone probe that allows for a surgeon to feel the interior side walls of the hole to locate any cracks or other unintended openings or irregularities along the interior of the hole and to further determine the exit point of the hole (i.e., for a hole that has been drilled entirely through the bone for subsequent placement of a bicortical screw or other fastener). The bone probe generally includes an elongated shaft slidably mounted within a body of the device serving as a handle adapted for manual manipulation. The elongated shaft of the probe includes a distal end configured to extend from the body of the device during use. The distal end includes a probing tip for contacting an interior portion of the hole. At least a portion of the elongated shaft may be substantially flexible or semi-rigid to provide a proper "feel" to the surgeon during examination of the hole in the bone. For example, the shaft of the bone probe may be substantially non-elastic such that the surgeon can apply pressure against the interior wall of the hole to feel for irregularities or the base of the hole via tactile feedback provided by the shaft. In some embodiments, the shaft may be tapered such that the shaft narrows in width or thickness in a direction towards the probing distal tip. In this manner, the flexibility of the shaft may increase along the shaft in a direction toward the probing tip.

The probing tip may include at least a first portion having a shape or contour that aids the surgeon in detecting surface irregularities (e.g., cracks, crevices, openings, etc.) on the interior surface of the hole. For example, in some embodiments the first portion may have a substantially arcuate or curved shape. The arcuate or curved portion may also aid the surgeon in locating the exit point (i.e., second opening) the hole so as to allow for the probing tip to be accurately placed and secured along an edge of the exit point so that the hole can be measured via the depth gauge member. The arcuate or curved shape of the first portion of the probing tip may generally lessen risk of tissue irritation that may otherwise occur along the interior surface of the hole, which is usually soft and easily penetrable with less curved and more abrupt surfaces (with sharp or distinct edges). In some embodiments, the first portion may have a general spherical shape. In other embodiments, the first portion may be substantially planar with rounded edges.

The probing tip also includes a second portion positioned opposite the first portion, wherein the second portion includes an engagement surface configured to pierce or otherwise establish purchase with an exterior portion of bone immediately adjacent to the exit point of the hole (i.e., along the edge of the hole). In particular, upon locating the exit point or second opening of the hole, the surgeon may then extend the probing tip through the exit point and then position the bone probe shaft against the interior surface of hole and pull back on the bone probe shaft so as to draw the probing tip, specifically the engagement surface, back towards, and into engagement with, the exterior surface of the bone along the edge of the exit point of the hole. Upon sufficient application of pressure (i.e., sufficient retraction of the bone probe shaft), the engagement surface of the probing tip engages and establishes purchase with the bone immediately adjacent the hole. Upon establishing engagement, the medical device may be stabilized in position, at which point, the depth gauge member can be used for measuring the depth of the hole. In some embodiments, the engagement surface may include surface texturing to enhance friction between the engagement surface and a portion of bone. For example, in some procedures in which a plate or implants is to be secured with screws through a bicortical drill hole, the probing tip may extend entirely through the hole (from one side of the bone to the other), at which point the surgeon may pull the bone probe back towards the hole such that the engagement surface of the second portion of the probing tip establishes purchase with one side of the bone, and the surface texturing enhances friction between the engagement surface and bone to reduce risk of slippage.

The bone probe is generally fixed to a handle of the device. The handle may include, for example, a proximal end including a grip portion to provide a surgeon with a means for applying a pulling force so as to draw the engagement surface of the probing tip of the bone probe into engagement with an exterior surface of bone immediately adjacent to a bicortical hole in the bone.

The depth gauge member is a cylinder that generally includes a hollow elongated body slidably mounted to a portion of the handle. The depth gauge cylinder includes a lumen in which at least a portion of the handle and the bone probe shaft are received within. The depth gauge cylinder is operable to slide along a longitudinal axis of the handle from an initial default position and an extended position relative to the handle. A tip member is releasably coupled to a distal end of the depth gauge cylinder and operable to correspondingly slide with the depth gauge cylinder during movement of the cylinder. The tip member includes an opening through which at least the bone probe shaft is received. The tip member further includes a distal end including a profile corresponding to an opening in a bone plate through which a screw is to be received. More specifically, the tip member of the present disclosure is particularly useful in procedures in which a depth measurement is to be obtained with a bone plate in place (i.e., positioned where it would be mounted). As generally understood, it is preferable to countersink a screw when performing a bone implant fixation procedure so as to avoid any potential complications as a result of a screw head extending from a surface of bone or a bone plate. There are known generally geometries of a countersink in a bone plate hole (for receiving the screw), which include at least a mini, small, and large fragment, wherein the mini-frag is the most common. The profile of the distal end of the tip member comprises a stepped profile including multiple distinct and separate stepped portions, wherein each stepped portion has a different diameter. Each of the separate stepped portions has a respective shape and/or diameter corresponding to a shapes and/or diameter of common countersink sizes provided in bone plates. The device further includes at least one sensor configured to generate an electronic signal indicative of a depth of the hole as a result of sensing a distance traveled by the depth gauge cylinder relative to the handle and bone probe For example, in one embodiment, upon establishing purchase with an exterior surface of bone generally providing an edge of the exit point of the drilled (or otherwise pierced hole) via the probing tip, a surgeon need only continue pulling back on the handle to thereby maintain engagement of the bone probe with the exterior surface of bone and then slide the depth gauge cylinder in a direction towards the bone. Upon sliding the depth gauge member towards the bone, at least a portion of the tip member will pass through an opening in the bone plate corresponding to the drilled hole until a portion of the stepped profile of the tip member makes contact with and engages a countersink portion of the opening in the bone plate. When the tip member is correctly positioned in the countersink of the bone plate, the most distal edge of the tip member will be aligned along the same plane as the bone-facing surface of the bone plate. The sensor is configured to generate an electronic signal based on the distance that the depth gauge cylinder traveled relative to the handle and bone probe, wherein the electronic signal is indicative of at least a depth of the hole. In particular, the sensor may include inductive or capacitive elements or assemblies configured to sense the location of a distal end of the depth gauge cylinder, for example, relative to a specific point along the handle, and, as a result, generate an electronic signal representing the distance there between as a result of movement (i.e., sliding) of the depth gauge cylinder. For example, the depth gauge cylinder may generally slide relative to the handle and bone probe between a most-proximal position and a most-distal position and a plurality of positions therebetween. As such, the depth gauge cylinder may be in the most-proximal position when in the default, initial position when depth measurement has not yet begun. Upon establishing engagement between the bone probe tip and the bone, the depth gauge cylinder may then be advanced in a direction towards the bone from the default, initial position until the tip member, specifically the stepped profile, makes contact with a countersink in the bone plate opening. The sensed distance traveled by the depth gauge cylinder is then used to calculate the depth of the hole. In particular, the device may include logic for determining hole depth based on known variables. For example, the length of the bone probe shaft extending from the distal end of the tip member when the depth gauge cylinder is in the initial, default position (i.e., the most-proximal position relative to the handle) may be known and programmed into the logic. As such, the sensed distance traveled by the depth gauge cylinder from the initial, default position until the tip member, specifically the stepped profile, makes contact with a countersink in the bone plate opening, may simply be subtracted from the known length of the bone probe shaft to thereby provide the depth of the hole.

Accordingly, the digital sensing of the hole depth provides a much more accurate measurement than conventional analog depth gauges and also requiring very little, if any, input or interpretation from the surgeon. Accordingly, by providing a much more accurate measurement of a hole depth, the surgeon is able to select the correct length screw for any given hole so as to improve the chances of a successful surgery.

In some embodiments, the device may further include a display provided on either the handle or the depth gauge cylinder and configured to visually provide a digital readout of a depth measurement of the hole based on the electronic signal from the sensor. In other embodiments, the device may be configured to wirelessly communicate and exchange data with a separate display or computing device, such as, for example, a monitor or panel display, a PC, a notebook, a tablet computer, a smartphone, or other wireless computing device.

Upon receiving the electronic signal from the sensor, the separate display or computing device may be configured to visually provide the depth measurement of the hole based on the electronic signal from the sensor. Furthermore, in some embodiments, the computing device may include a specific software application that may be directed to maintaining a record of the hole measurements and/or provide an interactive user interface in which multiple holes can be mapped to a particular plate or implant and the depth of each hole (including the thickness of the plate or implant) can be included and stored for records.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIGS. 10A and 10B illustrate retraction of the bone probe within the handle member and subsequent compression of a spring assembly upon movement of the handle towards the bone when the probing tip of the distal end of the bone probe shaft is in contact with the bottom of the drilled hole in the bone;

FIGS. 13A-13C illustrate a series of steps for performing a procedure of probing a fully drilled hole (i.e., a hole extending entirely through a bone for receipt of a bicortical bone screw) with the bone probe of FIG. 4 and further establishing purchase of the probing tip of the bone probe with a side of the bone adjacent to the bicortical drilled hole to secure the bone probe in place and allow the depth gauge member to be used for measuring the depth of the bicortical drilled hole.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a medical device for use in a bone implant fixation procedure and configured to provide a faster and more accurate measure of depth. In particular, the device includes a combination of a bone probe allowing for physical examination of a hole drilled in a bone and a depth gauge member for determining a depth of the hole and providing a digital measurement of the depth. Accordingly, the device of the present disclosure is capable of digitally measuring the depth of an opening in a bone during the same surgical step that a surgeon probes and inspects the interior of the opening.

Figure 1:
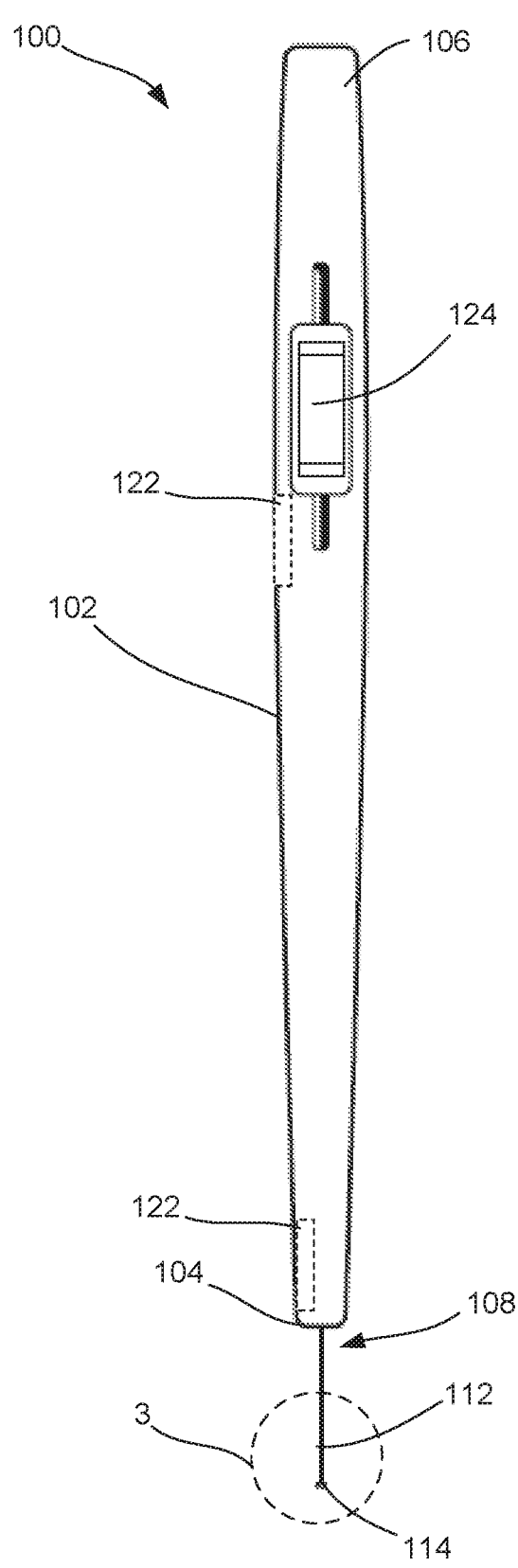
FIG. 1 is top view of one embodiment of a medical device consistent with the present disclosure.
Figure 2:
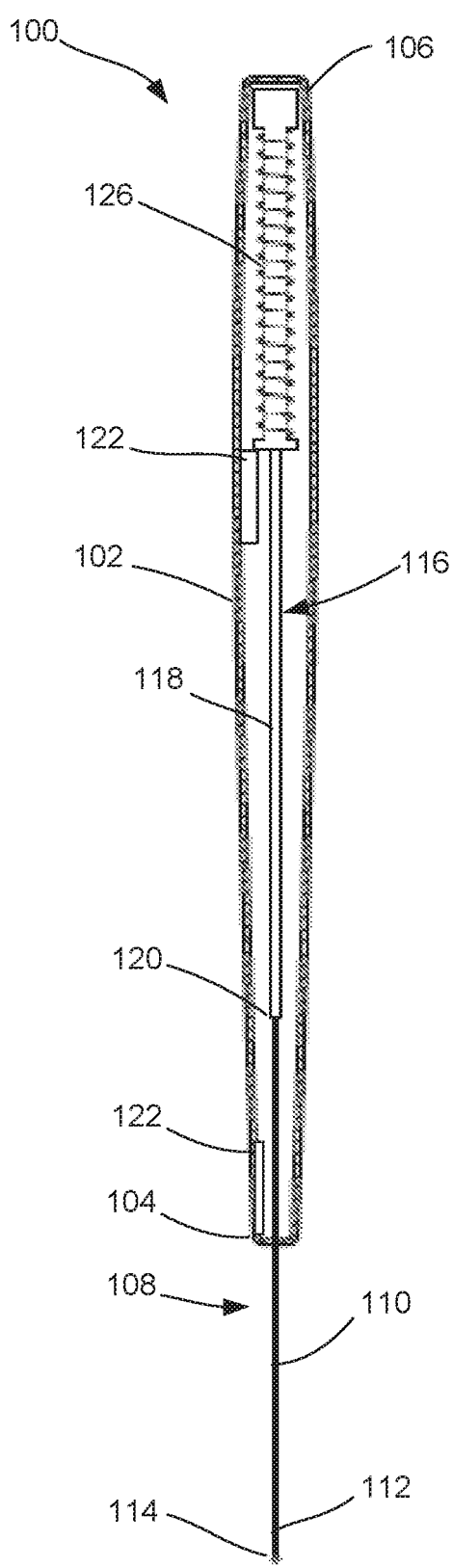
FIG. 2 is a cross-sectional view of the medical device of FIG. 1 illustrating the hollow interior of the handle and arrangement of the bone probe and depth gauge member relative to one another.

FIG. 1 is top view of one embodiment of a medical device 100 consistent with the present disclosure and FIG. 2 provides a cross-sectional view of the medical device 100. As shown, the medical device 100 includes a body 102 having a first end 104 and an opposing second end 106 and is generally hollow. The body 102 is configured as a handle and generally adapted for manual manipulation. Accordingly, the body will be referred to a "handle 102" hereinafter for ease of explanation.

The device 100 further includes a bone probe 108 slidably mounted within the handle 102. The bone probe 108 includes a shaft 110 having a distal end 112 configured to extend from, and retract towards, the first end 104 of the handle 102 during use, as will be described in greater detail herein. The distal end 112 further includes a probing tip 114, which is useful for examination and inspection of interior surfaces of a drilled hole in bone, as will be described in FIGS. 3A and 3B.

The device 100 further includes a depth gauge member 116 slidably mounted within the handle 102. The depth gauge member 116 generally includes a hollow elongated body 118 having a distal end 120 configured to extend from, and retract towards, the first end of the handle 102 during use, similar to the bone probe shaft 110, as will be described herein. The hollow elongated body 118 has a lumen in which at least a portion of the bone probe shaft 110 is received such that the bone probe 108 and depth gauge member 116 are independently slidable relative to one another and the handle 102. The device 100 further includes one or more depth measurement sensors 122 configured to generate an electronic signal indicative of a depth of at least the hole, wherein the electronic signal varies in relation to a distance between the first end 104 of the handle 102 and the distal end 120 of the depth gauge member 116, as will be described in greater detail herein.

The bone probe 108 and depth gauge member 116 may each be coupled to separate slider members for allowing a surgeon to manually control movement of the bone probe 108 and depth gauge member 116 independent of one another. For example, as shown in FIG. 1, a first slider 124 may be coupled to at least the bone probe shaft 110 and is slidable along a longitudinal axis of the handle 102, which such movement of the first slider 124 causes corresponding movement of the bone probe shaft 110. Although not shown in FIGS. 1 and 2, a second slider may be coupled to the depth gauge member 116 and is similarly slidable along the longitudinal axis of the handle 102, such that movement of the second slider causes corresponding movement of the depth gauge member 116.

The device 100 may further include a spring assembly 126 coupled to at least one of the bone probe 108 and depth gauge member 116. The spring assembly 126 may be configured to provide a biasing force upon at least one of the bone probe 108 and depth gauge member 116 so as to maintain either the bone probe 108 or depth gauge member 116 in a default extended position. For example, as shown in FIGS. 1 and 2, the bone probe 108 is generally positioned in an extended configuration (probing tip 114 extended out of first end 104 of handle 102), in which a surgeon may now examine an interior surface of a drilled hole, as is shown in FIGS. 10A and 10B.

During a bone-related procedure involving placement of a screw, or other fastener, it may be desirable to determine whether drilling of the hole resulted in any cracks or openings, either along an interior side wall of the hole or at the base of the hole. Ensuring the integrity of the drilled hole is important because unintended cracks, openings, or irregularities can increase the risk that the screw will either not securely attach itself within the hole or may result in chipping or fragmenting of bone during fastening of the screw within the hole. It is generally not possible for a surgeon to visual examine the integrity of the drilled hole due to a limited field of view within the hole (drilled holes can be relatively small in width, such as 5 mm or less in some instances).

The bone probe 108 allows for a surgeon to feel the interior side walls and bottom of a drilled hole so as to locate any cracks or other unintended openings or irregularities along the interior of the hole. For example, probing tip 114 is configured for contacting an interior portion of the hole and at least a portion of the elongated shaft 110 may be substantially flexible or semi-rigid to provide a proper "feel" to the surgeon during examination of the hole in the bone. For example, the shaft 110 of the bone probe 108 may be substantially non-elastic such that the surgeon can apply pressure against the interior wall of the hole to feel for irregularities or the base of the hole via tactile feedback provided by the shaft 110. In some embodiments, the shaft 110 may be tapered such that the shaft narrows in width or thickness in a direction towards the probing distal tip. In this manner, the flexibility of the shaft may increase along the shaft in a direction toward the probing tip 114.

Figure 3A:
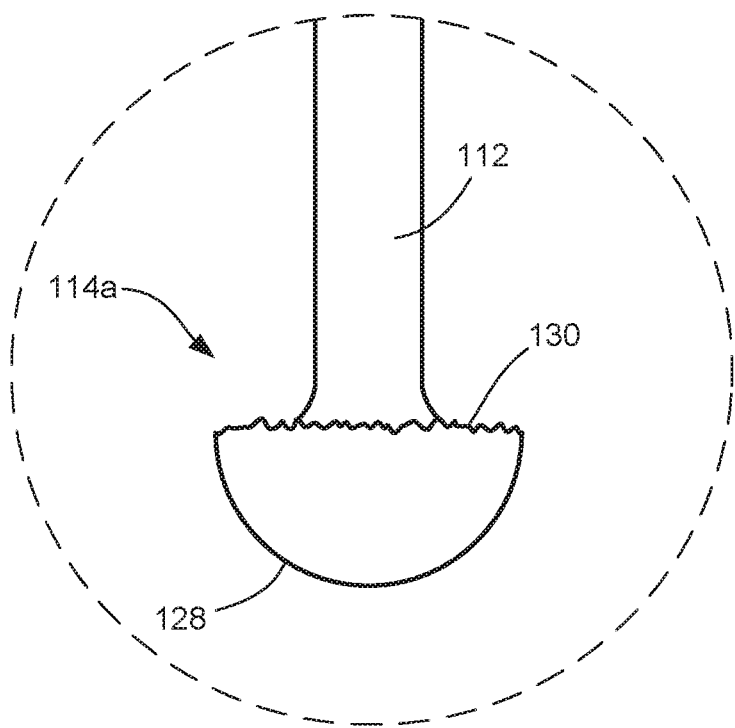
FIGS. 3A and 3B are enlarged front and side views, respectively, of one embodiment of a probing tip defined on the distal end of the bone probe shaft.
Figure 3B:
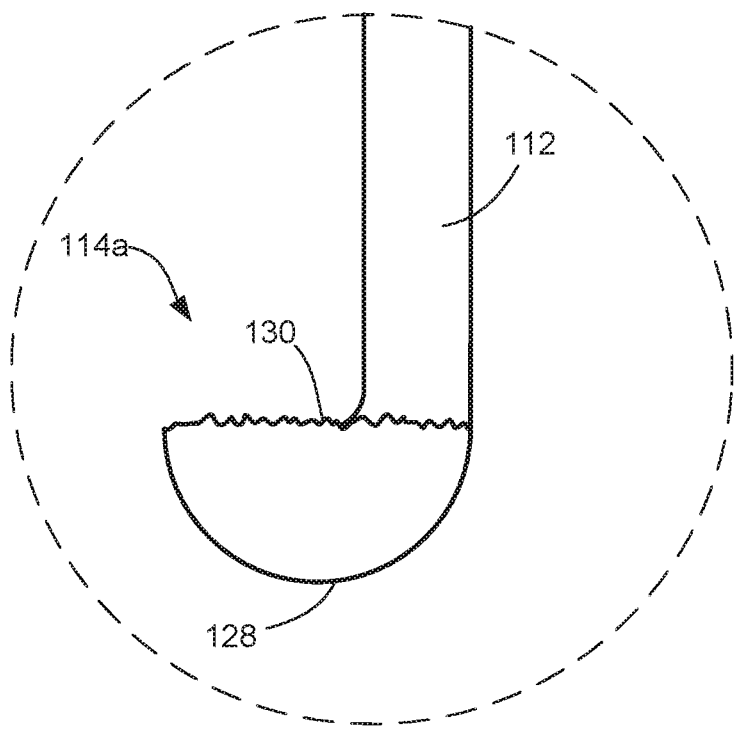

FIGS. 3A and 3B are enlarged front and side views, respectively, of one embodiment of a probing tip 114a defined on the distal end 112 of the bone probe shaft 110. As shown, the probing tip 114a may include an arcuate first portion 128 shaped and configured to contact an interior surface of the hole with little or no resistance and provide tactile feedback of the interior surface to the surgeon. For example, as shown, the first portion 128 is substantially curved or spherical so as to prevent or minimize the risk that the probing tip 114a would penetrate or otherwise engage of portion of the interior surface of the hole. Rather, the first portion 128 is shaped so as to glide or easily slide along the interior surface, while still allowing sufficient contact to provide tactile feedback to the surgeon. Accordingly, the arcuate first portion 128 may lessen or eliminate tissue irritation that may otherwise occur when a sharper object is used to probe the bone opening.

The probing tip 114a further includes a second portion 130 having an engagement surface shaped and configured to establish purchase with a portion of the interior surface of the hole and associated with a bottom of the hole upon sufficient application of force to the shaft. The engagement surface may be a substantially abrupt edge of the probing tip 114, in which the transition between the first portion 128 and second portion 130 is sudden (e.g., sharp corner or edge). Accordingly, upon sufficient pressure, the engagement surface is configured to pierce or establish purchase with tissue in the interior of the hole. Thus, the probing tip 114a is multifunctional in that the first portion 128 allows for probing of the interior surfaces to provide a surgeon with a "feel" for examination purposes and to further locate the bottom of the hole and the second portion 130 allows for the surgeon to establish purchase at the desired site (i.e., the bottom of the hole) so as to stabilize the bone probe in the desired position, at which point, the depth gauge member can be used for measuring the depth of the hole.

In some embodiments, the engagement surface of the second portion 130 may include surface texturing to enhance friction between the engagement surface and a portion of bone. For example, in some procedures in which a plate or implants is to be secured with screws through a bicortical drill hole, the probing tip may extend entirely through the hole (from one side of the bone to the other), at which point the surgeon may pull the bone probe back towards the hole such that the engagement surface of the second portion of the probing tip establishes purchase with one side of the bone, and the surface texturing enhances friction between the engagement surface and bone to reduce risk of slippage.

Figure 3C:
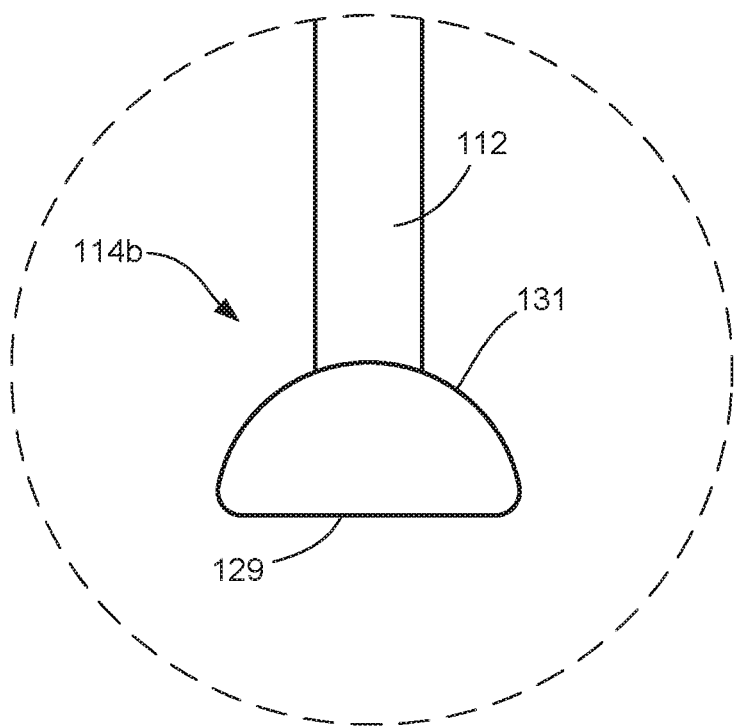
FIGS. 3C and 3D are enlarged front and side views, respectively, of another embodiment of a probing tip defined on the distal end of the bone probe shaft.
Figure 3D:
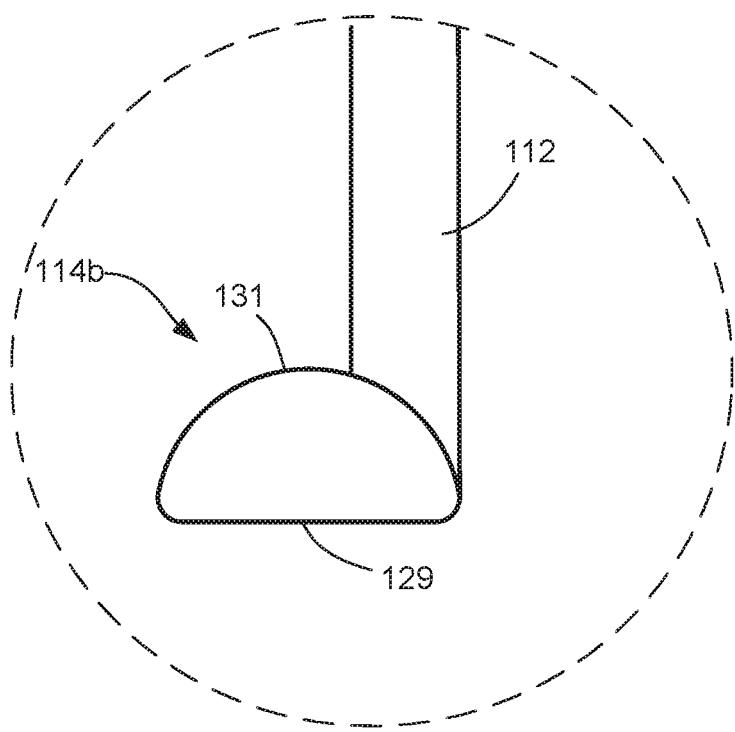

FIGS. 3C and 3D are enlarged front and side views, respectively, of another embodiment of a probing tip 114b defined on the distal end 112 of the bone probe shaft 110. As shown, the probing tip 114b may include a first portion 129 shaped and configured to contact an interior surface of the hole with little or no resistance and provide tactile feedback of the interior surface to the surgeon. For example, as shown, the first portion 129 has a substantially planar or flat surface with rounded edges so as to prevent or minimize the risk that the probing tip 114b would penetrate or otherwise engage of portion of the interior surface of the hole. Rather, the rounded edges of the first portion 129 are shaped so as to glide or easily slide along the interior surface, while still allowing sufficient contact to provide tactile feedback to the surgeon. The substantially planar surface may yield a more accurate depth measurement than a full radius bottom in that, in some circumstances, the flat surface may provide better engagement and sit more flush with the bottom of the hole than the full radius first portion 128 of probing tip 114a (in FIGS. 3A and 3B). It should be noted, however, that the round edges may still provide enough edge to serve as an engagement surface for establishing purchase with a portion of the interior surface of the hole and associated with a bottom of the hole upon sufficient application of force to the shaft. The second portion 131 of probing tip 114b may be substantially curved or spherical.

Figure 4:
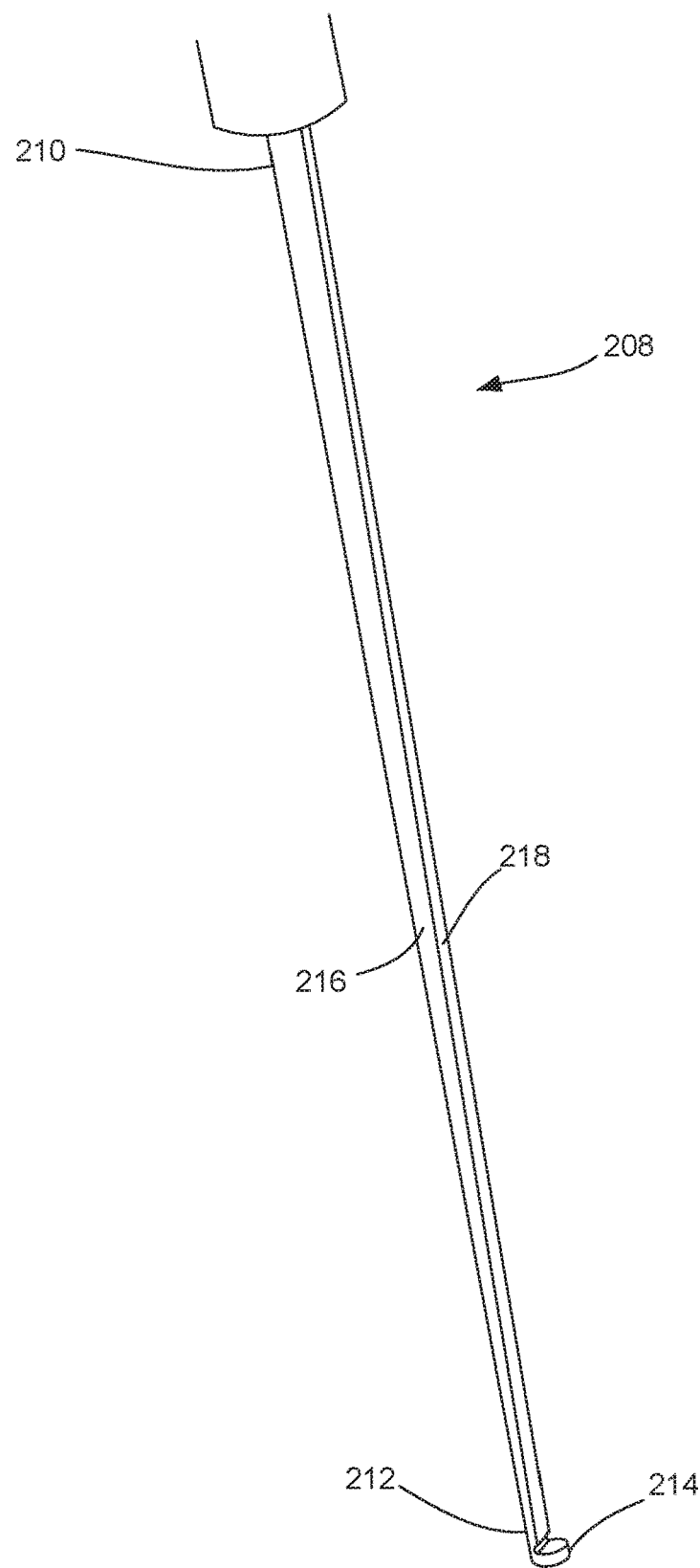
FIG. 4 is a perspective view of another embodiment of a bone probe compatible for use with the medical device of FIG. 1, illustrating another embodiment of a probing tip defined on a distal end of the bone probe shaft.

FIG. 4 is a perspective view of another embodiment of a bone probe 208 compatible for use with the medical device 100 consistent with the present disclosure. Similar to the bone probe 108 previously described herein, the bone probe 208 allows for a surgeon to feel the interior side walls of a hole to locate any cracks or other unintended openings or irregularities along the interior of the hole and, in combination with the depth gauge member 116, the bone probe 208 further allows for depth measurements of the hole. In particular, as described in greater detail herein, the bone probe 208 is configured for assisting in measuring of a drilled hole extending entirely through a bone (i.e., a bicortical drilled hole) in which a bicortical screw or other bicortical fastener is to be placed. Accordingly, unlike the bone probe 108, which has a bone probing tip generally configured to locate the base or bottom of a drilled hole in bone that does not extend entirely through the bone, the bone probe 208 includes a bone probing tip specifically configured to be extended entirely through a drilled hole (from one side of the bone to the other), at which point the surgeon may pull the bone probe back towards the hole such that an engagement surface of the bone probing tip establishes purchase with one side of the bone, thereby anchoring or securing the bone probe 208 in place and allowing subsequent depth measurement of the hole via the depth gauge member in a manner described previously herein.

The bone probe 208 includes a shaft 210 having a proximal end 211 and an opposing distal end 212 configured to extend from, and retract towards, the first end 104 of the handle 102 during use, as will be described in greater detail herein. The proximal end 211 may further include a cut out portion (or notch) 213 allowing for the bone probe shaft 210 to be physically coupled to a control mechanism or the like (e.g., the slider 124) for extending/retracting the shaft 210. The distal end 212 includes a probing tip 214, which is useful for examination and inspection of interior surfaces of a drilled hole in bone in a similar manner as the probing tip 114.

The bone probe 208 allows for a surgeon to feel the interior side walls of a drilled hole so as to locate any cracks or other unintended openings or irregularities along the interior of the hole. For example, probing tip 214 is configured for contacting an interior portion of the hole and at least a portion of the elongated shaft 210 may be substantially flexible or semi-rigid to provide a proper "feel" to the surgeon during examination of the hole in the bone. For example, the shaft 210 of the bone probe 208 may be substantially non-elastic such that the surgeon can apply pressure against the interior wall of the hole to feel for irregularities or the base of the hole via tactile feedback provided by the shaft 210.

In some embodiments, the shaft 210 may be tapered such that the shaft narrows in width or thickness in a direction towards the probing distal tip 214. In this manner, the flexibility of the shaft may increase along the shaft 210 in a direction toward the probing tip 214. For example, in the illustrated embodiment, the shaft 210 may have a generally cylindrical geometry along a majority of its length and may include a substantially planar portion formed along a length thereof and tapered in a direction towards the distal end 212. For the purposes of discussion, and ease of description, the following description refers to the shaft 210 as having a first side 216 including the cylindrical shape and a second side 218 that is substantially planar and extends along length of the shaft 210, the shaft tapering in thickness (i.e., transitioning from greater thickness to less thickness along length of the shaft 210) from the proximal end 211 to the distal end 212, as illustrated in FIGS. 5 and 6.

Figure 5:
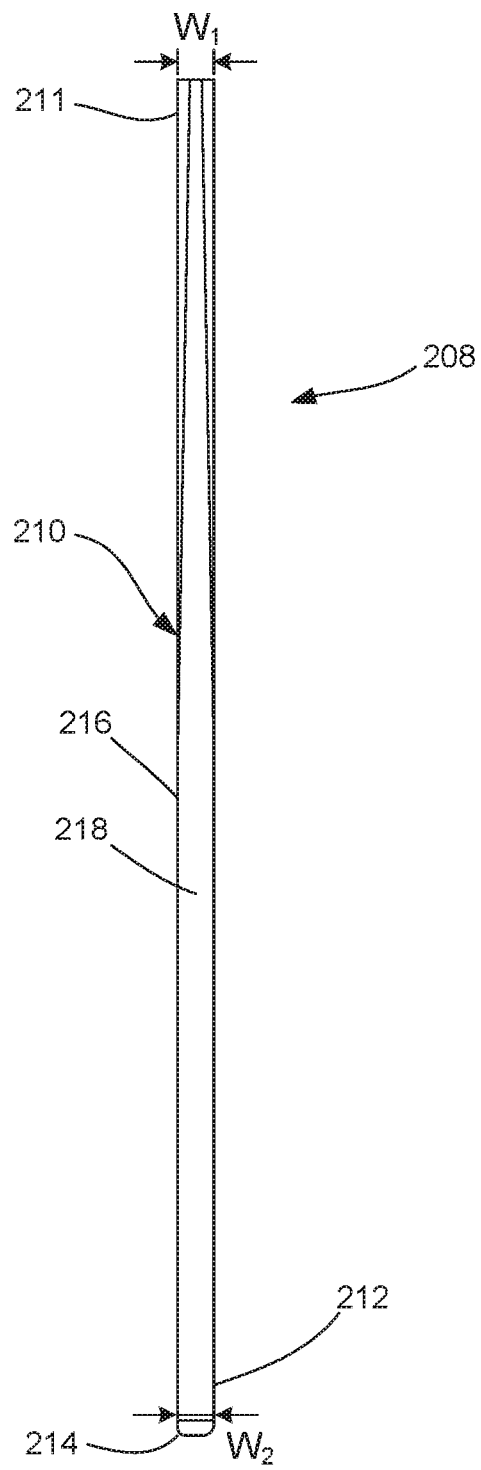
FIGS. 5 and 6 are front and side views, respectively, of the bone probe of FIG. 4.
Figure 6:
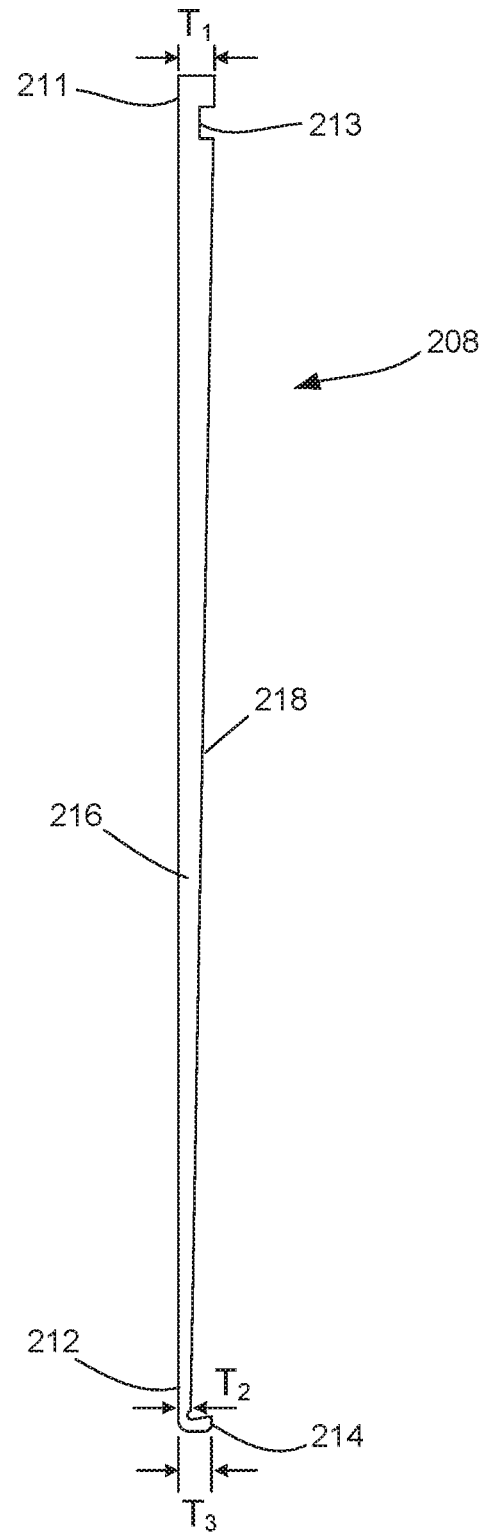

In particular, FIG. 5 is a front view (i.e., facing in a direction towards the second side 218 of the shaft) of the bone probe 208 and FIG. 6 is a side view of the bone probe 208. As shown in FIG. 5, the overall width of the shaft 210 remains relatively constant from the proximal end 211 to the distal end 212, while the thickness of the shaft 210 tapers from the proximal end 211 towards the distal end 212, as shown in FIG. 6. For example, the bone probe 208 may be formed from a single cylindrical piece of medical grade material (e.g., a rod of a metal such as stainless steel, nitinol, or aluminum). The second side 218 may be formed by way of a subtractive manufacturing process, such as grinding, milling, or the like, to thereby remove material from the shaft 210 to form the substantially planar surface of the second side 218. Furthermore, the probing tip 214 is further formed by way of grinding, milling, or other technique for removing material from the shaft 210 so as to form the hook-like design, as will be described with reference to FIGS. 7, 8, and 9 in greater detail herein. Accordingly, as shown in FIG. 5, the width $W_1$ at the proximal end 211 is approximately equal to the width $W_2$ at the distal end 212 and the probing tip 214. As shown in FIG. 6, the thickness $T_1$ at the proximal end 211 is greater than the thickness $T_2$ at the distal end 212, while thickness $T_1$ is approximately equal to the thickness $T_3$ at the probing tip 214. Accordingly, the tapering in thickness of the shaft 210 occurs along the substantially planar second side 218 as a result of the formation of the second side 218 (i.e., machining to remove shaft material and create the substantially planar surface).

Figure 7:
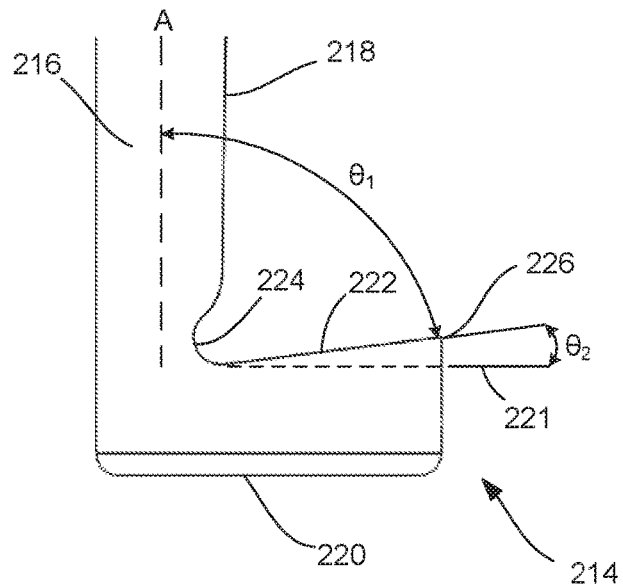
FIG. 7 is an enlarged side view of the probing tip of FIG. 4.
Figure 8:
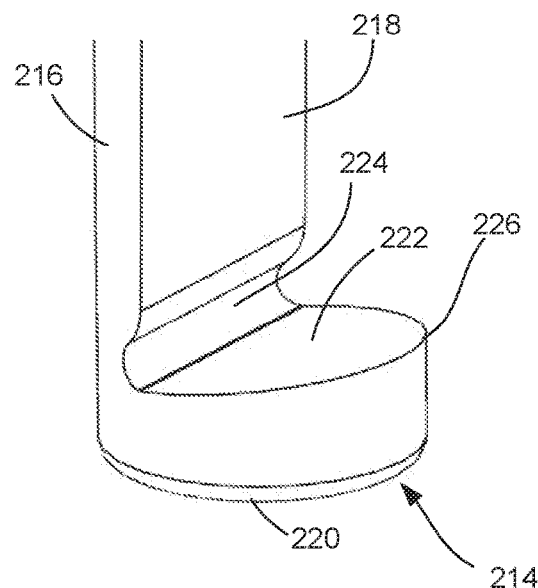
FIGS. 8 and 9 are enlarged perspective views of the probing tip of FIG. 4.
Figure 9:
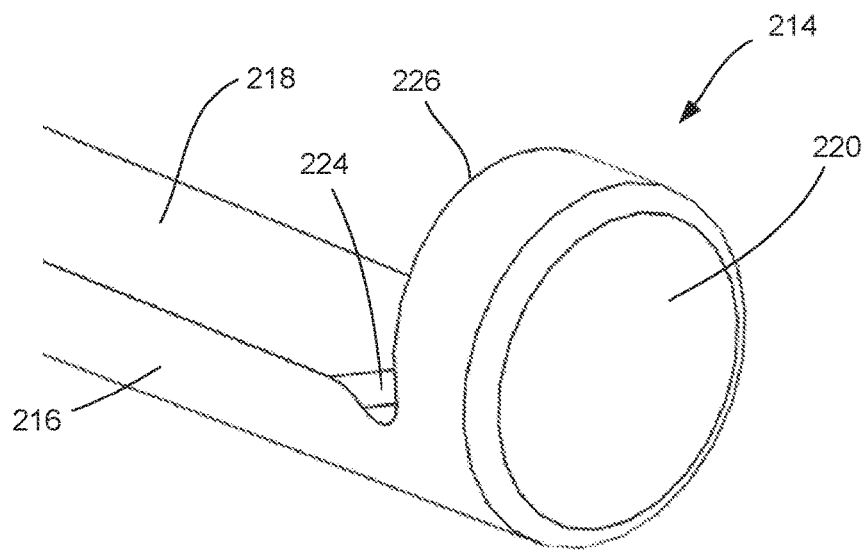

FIG. 7 is an enlarged side view of the probing tip 214 and FIGS. 8 and 9 are enlarged perspective views of the probing tip 214. As shown, the probing tip 214 may generally resemble a hook or the like extending from the distal end 212 of the probe shaft 210 and oriented at an angle relative to the shaft 210, wherein such angle may be approximately perpendicular to the longitudinal axis of the shaft 210. However, it should be noted that the probing tip 214 may be oriented at obtuse angle or an acute angle relative to the longitudinal axis of the shaft 210. The probing tip 214 may include a base portion 220 shaped and configured to contact an interior surface of the hole with little or no resistance and provide tactile feedback of the interior surface to the surgeon. For example, as shown, the base portion 220 may have substantially curved or arcuate edges so as to prevent or minimize the risk that the probing tip 214 would penetrate or otherwise engage of portion of the interior surface of the hole. Rather, the base portion 220 may be shaped so as to glide or easily slide along the interior surface, while still allowing sufficient contact to provide tactile feedback to the surgeon. Accordingly, the base portion 220 may lessen or eliminate tissue irritation that may otherwise occur when a sharper object is used to probe the bone opening.

The probing tip 214 further includes a top portion 222 having a substantially planar surface that is oriented at a first angle $\theta_1$ relative to a longitudinal axis A of the shaft 210 and further oriented at a second angle $\theta_2$ relative to a plane 221 along which the base portion 220 is substantially parallel to. In some embodiments, the surface of the top portion 222 may be substantially perpendicular to axis A, and thus the angle $\theta_1$ may be approximately 90 degrees. However, in some embodiments, the surface of the top portion 222 may be oriented at an angle offset relative to axis A. For example, as shown in FIGS. 7-9, the angle $\theta_1$ may be acute (i.e., less than 90 degrees). In some embodiments, the angle $\theta_1$ may be between 1 and 89 degrees. In some embodiments, the angle $\theta_1$ may be between 5 and 25 degrees. However, in some embodiments, the angle $\theta_1$ may be obtuse (i.e., greater than 90 degrees). In some embodiments, the angle $\theta_1$ may be between 91 and 179 degrees. In some embodiments, the angle $\theta_1$ may be between 95 and 115 degrees. With reference to second angle $\theta_2$, in some embodiments, the surface of the top portion 222 may be substantially parallel to the plane 221, and thus the angle $\theta_2$ is approximately 0 degrees. However, in some embodiments, the surface of the top portion 222 may be oriented at an angle offset relative to plane 221. For example, as shown in FIGS. 7-9, the surface of the top portion 222 may be offset relative to the plane 221 and thus the angle $\theta_2$ may be between approximately 1 and 89 degrees. In some embodiments, the angle $\theta_2$ is may be between approximately 5 and 25 degrees.

The probing tip 214 further includes a groove or notch 224 formed adjacent to the distal end 212 of the probe shaft 210, thereby resulting in less shaft material present at the junction between the probing tip 214 and the distal end 212 of the shaft 210, which allows for increased deflection of the tip 214 relative to the shaft 210 for improving the purchasing the tip 214 with a portion of the bone, as will be described in greater detail herein. The probing tip 214 further includes an engagement surface 226, in the form of an edge, defined along the perimeter of the top portion 222. The engagement surface 226 is shaped and configured to establish purchase with a portion of the bone, specifically a side of the bone immediately adjacent to an opening of the drilled hole through which the probing tip has passed. In particular, as will be described in greater detail herein, upon an operator extending the probing tip 214 entirely through a bicortical drilled hole (i.e., a drilled hole extending entirely from one side of the bone through to the opposing side of the bone), the engagement surface 226 is shaped and configured to establish purchase with a portion of the opposing side of the bone immediately adjacent to the opening of the drilled hole in response to manipulation from the surgeon. The engagement surface 226 may be a substantially abrupt edge of the probing tip 214, in which the transition between the base portion 220 and the top portion 222 is sudden (e.g., sharp corner or edge). Accordingly, upon sufficient pressure, the engagement surface 226 is configured to pierce or establish purchase with a portion of the opposing side of bone, thereby securing the bone probe shaft 210 in place for subsequent depth measurements.

Thus, the probing tip 214 is multifunctional in that the base portion 220 allows for probing of the interior surfaces to provide a surgeon with a "feel" for examination purposes and to further locate the opposing side of the bone and the top portion 222 allows for the surgeon to establish purchase at the desired site (i.e., portion of the opposing side of the bone adjacent to the opening of the drilled hole) so as to stabilize the bone probe in the desired position, at which point, the depth gauge member can be used for measuring the entire depth of the hole. In some embodiments, the engagement surface 226 of the top portion 222 may include surface texturing to enhance friction between the engagement surface 226 and the portion of bone to reduce risk of slippage during bicortical depth measurements.

Furthermore, as previously described, the groove 224 present at the junction between the distal end 212 of the probe shaft 210 and the probing tip 214 allows for increased deflection of the tip 214 relative to the shaft 210 for improving the purchasing of the portion of bone adjacent to the hole opening with the tip 214. For example, upon advancing the probing tip 214 entirely through the hole, the surgeon may then position the substantially planar second side 218 against the interior surface of the drilled hole and then retract (i.e., pull back) the probe shaft 210 such that the top portion 222 of the probing tip 214 comes into contact with a portion of the opposing side of the bone immediately adjacent to the opening of the hole. As the surgeon is pulling the bone probe shaft 210 back towards the hole, the groove 224 will allow for additional flexing of the probing tip 214 relative to the remainder of the probe shaft 210 due to less material at the junction between the shaft 210 and the tip 214 at the groove 224, which will improve the purchasing or grabbing of the opposing side of the bone with the engagement surface 226 of the top portion 222 of the probing tip. Furthermore, the tapered thickness of the shaft 210, provided by the substantially planar second side 218, allows for deflection or bending of the shaft 210 on one axis, such that, if the probing tip 214 is substantially perpendicular to shaft 210, as generally shown, application of pressure upon the shaft 210 results in deflection of the probing tip 214, particularly the engagement surface 226, to become angled upward, thereby enabling a superior purchase or gripping of the outer surface of the opposing side of the bone.

It should be noted that the bone probe 208 may also be used for obtaining depths of drilled holes that are not bicortical (i.e., that do not extend entirely through the bone from one side to the other side). For example, the engagement surface 226 may establish purchase with a portion of the interior surface of the hole and associated with a bottom of the hole upon sufficient application of force to the shaft 210 and subsequently the tip 214. The engagement surface 226 may be a substantially abrupt edge of the probing tip 114, in which the transition between the base portion 220 and the top portion 222 is sudden (e.g., sharp corner or edge). Accordingly, upon sufficient pressure, the engagement surface 226 is configured to pierce or establish purchase with tissue in the interior of the hole. Accordingly, upon placement of force against the probing tip 214, such as when a surgeon presses the probing tip 214 against an interior portion of the hole, the groove 224 will allow for additional flexing of the probing tip 214 relative to the remainder of the probe shaft 210 due to less material at the junction between the shaft 210 and the tip 214 at the groove 224, which will improve the purchasing or grabbing of a surface of the hole via the engagement surface 226. Furthermore, the tapered thickness of the shaft 210, provided by the substantially planar second side 218, allows for deflection or bending of the shaft 210 on one axis, such that, if the probing tip 214 is substantially perpendicular to shaft 210, as generally shown, application of pressure upon the shaft 210 results in deflection of the probing tip 214, particularly the engagement surface 226, to become angled upward, thereby enabling a superior purchase or gripping of the interior surface of the hole.

FIGS. 10A and 10B illustrate an initial process of examining, via the bone probe 108, a drilled hole 134 in a bone 132. For example, as previously described herein, the biasing force from the spring assembly 126 may be sufficient so as to maintain the bone probe 108 in the extended position while the surgeon probes an interior surface 136 of the drilled hole 134 and locates the bottom 138 of the hole 134. However, as shown in FIG. 10B, the biasing force may be overcome upon a surgeon moving the handle 102 in a direction towards the hole 134 once the desired target site is located, such as locating the bottom 138 of the hole 134. The surgeon can move the handle 102 until the first end 104 of the handle 102 abuts either the surface of the bone 132 or a surface of a plate or implant 140, as indicated by arrow 142, thereby resulting in compression of the spring assembly 126 while maintaining placement of the probing tip 114 at the bottom 138 of the hole 134, as indicated by arrow 144. At this point, the depth gauge member 116 can be advanced in a direction towards the hole 134, such that the hollow shaft 118 slides over the bone probe shaft 110, wherein the bone probe shaft 110 generally acts as a guide and holding position as a result of the engagement surface of the second portion 130 of the probing tip 114 having established purchase with the bottom 138 of the hole 134. The depth gauge member 116 can be extended down into the hole 134 until the distal end 120 of the depth gauge member 116 abuts the bottom 138 of the hole 134. Accordingly, the one or more depth measurement sensors 122 can then generate an electronic signal in relation to a distance between the first end 104 of the handle 102 and the distal end 120 of the depth gauge member 116, wherein the electronic signal is indicative of the depth of the hole 134 and the thickness of the plate or implant 140.

The device 100 of the present disclosure may include a variety of different sensing devices suitable for determining a length or depth of the drilled hole or bore to be measured. For example, the one or more depth measurement sensors 122 may include, but are not limited to, an electromechanical or electronic sensor, such as a linear encoder, and may employ any one or more of acoustic, ultrasound, capacitive, electric field, inductive, electromagnetic (e.g., Hall effect-type) and optical components for determining relative or absolute distance measurements. In some embodiments, the sensors 122 may be configured to measure, sense, discriminate, or otherwise determine a length or distance between at least the first end 104 of the handle 102 and the distal end 120 of the depth gauge member 116.

For example, in one embodiment, as shown in FIGS. 10A and 10B, at least a first sensor element 122a is positioned proximate to the first end 104 of the handle 102 and a second sensor element 122b is positioned on the depth gauge shaft 118 proximate the distal end 120. The sensor elements 122a, 122b are configured to measure at least one of relative, absolute and incremental movement (e.g., distance, speed, etc.) of the depth gauge shaft 118 with respect to the first end 104 of the handle 102 during a measurement procedure. For example, in one embodiment, the sensor elements 122a, 122b may be used for measure an absolute distance that the depth gauge 116 distal end 120 is moved relative to the fixed reference point such as, for example the first end 104 of the handle 102.

The first sensor element 122a may be an active inductive, capacitive or optical element that is in communication with circuitry (e.g., a controller) of a user interface portion of the device (e.g., a GUI display or the like with user inputs). The first sensor element 122a may include one or more longitudinally-extending conductors that are wires, cables or traces on a printed circuit board such as, for example, a flex-circuit or the like. Furthermore, the first sensor element 122a may further include a plurality of inductive, capacitive or optical elements that may be coupled with and disposed on the longitudinally-extending conductors. The second sensor element 122b may be configured on the depth gauge shaft 118 in manner so as to cooperate with the first sensor element 122a proximate the first end 104 of the handle 102. For example, the second sensor element 122b may be a generally passive element such as a permanent magnet, optical element (e.g., indicia) or the like that is configured to cooperate, communicate or otherwise interact with the first sensor element 122a. For example, during a measurement procedure, movement of the depth gauge 116 out of the device handle 102 results in interaction between the first and second sensor elements 122a, 122b. In particular, as the depth gauge 116 extends from the device handle 102, the first and second sensor elements 122a, 122b move relative to one another (i.e., second sensor element 122b moves past first sensor element 122a and, in combination with one another, provide signals (e.g., pulses, etc.) to the circuitry, which processes the signals and displays a distance measurement on a display and/or transmits the signals to separate computing devices.

In various embodiments of the present invention, the one or more sensors 122 may be connected with a microprocessor and/or other digital electronic device in order to produce an output for an electronic display, such as a liquid crystal display or light-emitting diode display, and or for wireless/wired transmission of electronic signals, comprising the measurement data, to a wireless compatible computing device. For example, in some embodiments, the microprocessor or other digital electronic device may be connected to a wireless transmitter for wireless transmission of electronic signals. In some embodiments, a signal conditioning circuit may interpose the inductive or capacitive elements of the electronic sensor and the microprocessor or other digital electronic device used to drive the display, thus ensuring that correct input current and voltage levels are provided to the various components. The device may further include a power source, such as a primary or secondary battery, may be connected to the signal conditioning circuit or to the microprocessor directly.

It should be noted that the device 100 of the present disclosure may include a variety of different electronic sensor and circuitry assemblies for determining and transmitting depth measurements, including the sensors and systems discussed in U.S. Pat. Nos. 7,165,336; 7,444,756; 7,493,703; 7,607,238; 7,676,943; 7,685,735; 7,730,629; 7,895,762; 7,895,767, the contents of each of which are hereby incorporated by reference in their entirety.

Figure 11:
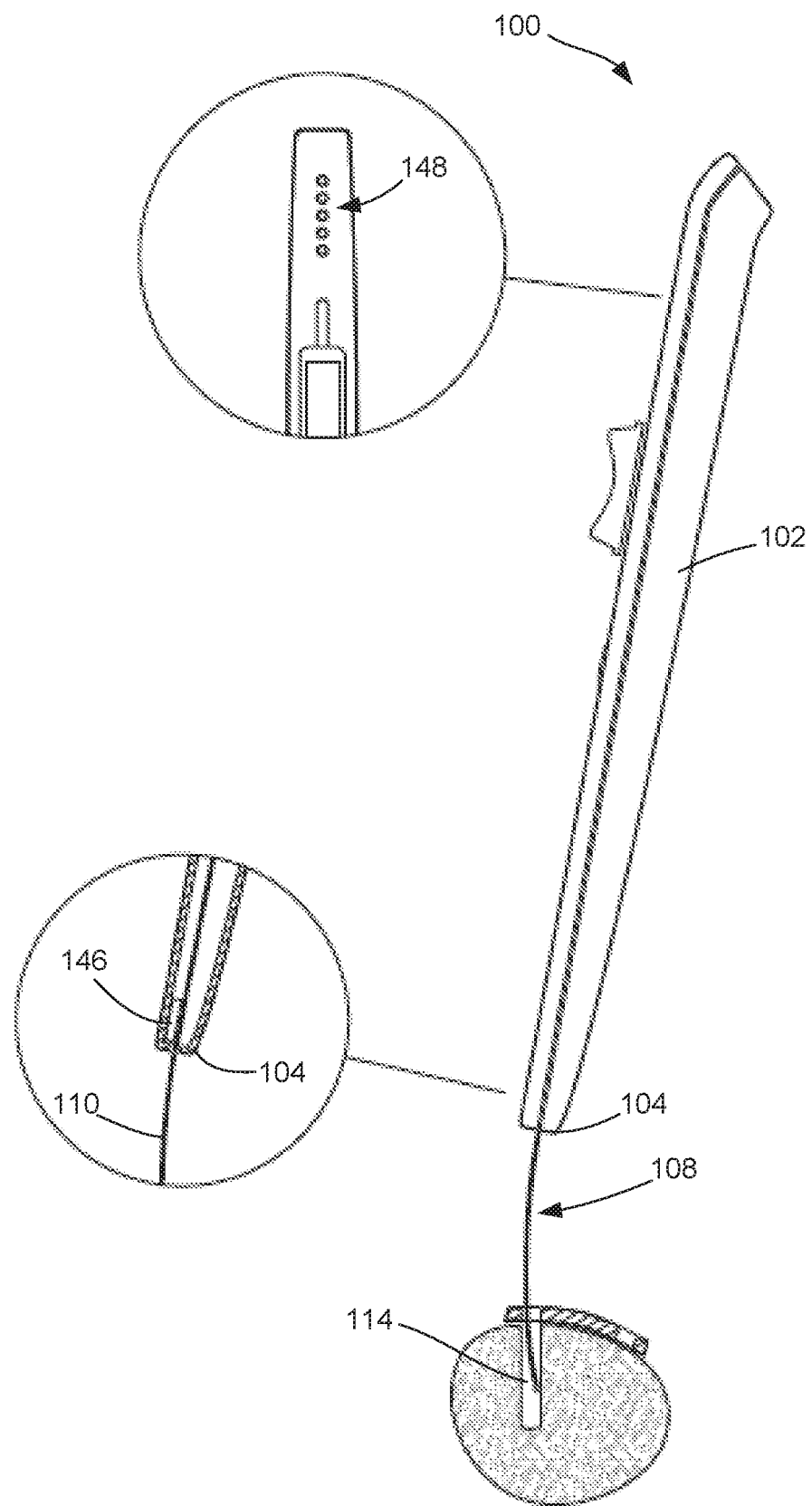
FIG. 11 is a side view of the medical device of FIG. 1 including a strain sensor sensing strain upon the bone probe shaft and providing an electronic signal indicative of the strain to an audio or visual component for providing an audible or visual alert.

FIG. 11 is a side view of the medical device 100 including a strain sensor 146 for sensing strain upon the bone probe shaft 110 as a result of probing the interior surface of a drilled hole. The sensor 146 may include a strain gauge or the like configured to determine a strain of the bone probe shaft 110, which may be useful for alerting the surgeon of an amount of resistance that the distal probing tip 114 is encountering during probing of the interior of the hole. For example, while a surgeon may be able to "feel" the interior surface and further have a sense of when the probing tip 114 actually makes contact with the bottom of the hole, the strain sensor 146 may further generate an electronic signal based on a sensed strain of the shaft 110 which may then be used to provide an audible and/or visual alert, via a device 148 (i.e., speaker or lights) to the surgeon indicating that the probing tip 116 is in fact positioned at the bottom of the hole.

For example, the resistance encountered when the probing tip 116 engages the bottom of the hole may have a certain strain value (i.e., above a certain threshold) which may be different than a resistance encountered with the sidewalls of the hole (which may have a softer, spongier tissue). Accordingly, the audible and/or visual alert may confirm to a surgeon whether they are in fact positioned at the bottom of the hole or if too much pressure is being placed against the interior surface such that they risk possibly inadvertently piercing the interior surface.

Figures 12A, 12B, 12C, 12D, 12E, 12F:
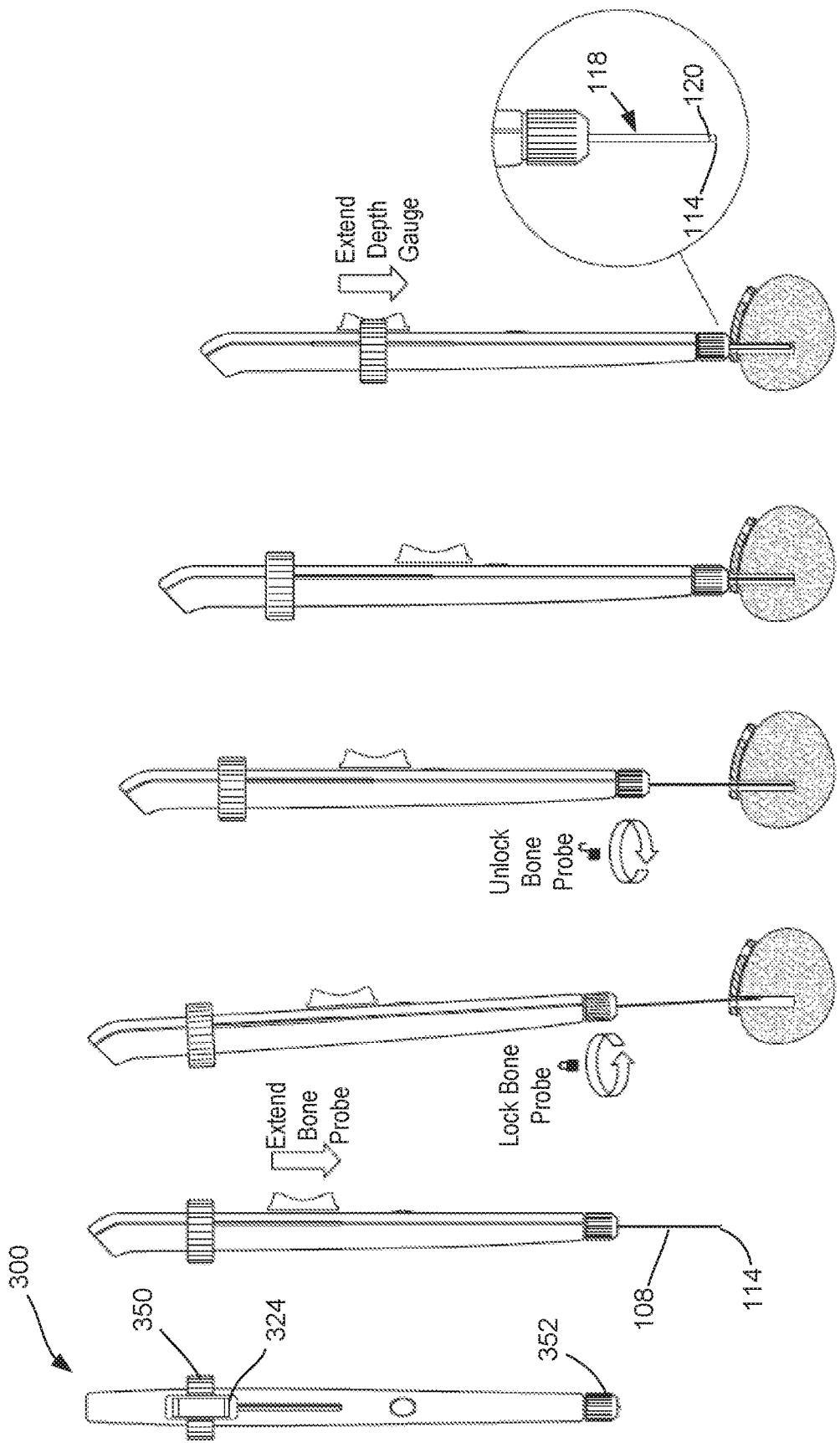
FIGS. 12A-12F illustrate a series of steps for performing a procedure of probing a drilled hole and subsequently obtaining a depth measurement using another embodiment of a medical device consistent with the present disclosure.

FIGS. 12A-12F illustrate a series of steps for performing a procedure of probing a drilled hole and subsequently obtaining a depth measurement using another embodiment of a medical device 300 consistent with the present disclosure. As shown, the device 300 may be similarly configured as device 100 previously described herein. However, as shown in FIG. 12A, both the bone probe 108 and depth gauge member 116 may both be completely withdrawn into the handle 102 until either a first slider 324 is moved, resulting in corresponding movement of the bone probe 108, or a second slider 350 is moved, resulting in corresponding movement of the depth gauge member 116, as shown in FIG. 12E.

In addition to including sliders for allowing independent movement of the bone probe and depth gauge member, the device 300 further includes a locking member 352 for locking a position of at least the bone probe 108. As shown, the locking member 352 is coupled to the first end 104 of the handle 102 and is associated with at least the bone probe 108 in such as manner so as to allow/prevent movement of the bone probe 108. For example, the locking member 352 has an unlocked configuration and a locked configuration, wherein, in the unlocked configuration, the locking member 352 allows the bone probe 108 to freely move and, when in the locked configuration, the locking member 352 prevents movement of the bone probe 108.

For example, upon extending the bone probe 108, a surgeon may then place the locking member 352 in a locked configuration, as shown in FIG. 12C, in which the locking member 352 is configured to provide sufficient contact with the bone probe shaft 110 so as to prevent, or make difficult, the movement of the bone probe shaft 110 relative to the first end 104 of the handle 102, thereby providing an amount of rigidity to the probe shaft 110. Accordingly, a surgeon may now perform examination of a drilled hole without concern of the bone probe 108 withdrawing back into the handle 102 or being loose.

Upon locating the base or bottom of the hole, the surgeon may then apply sufficient force upon the bone probe shaft 110 so that the engagement surface of the second portion of the probing tip engages and establishes purchase with the bottom of the hole, or a sidewall immediately adjacent to the bottom, as shown in FIG. 12D. Upon establishing engagement, the surgeon may then place the locking member 352 in an unlocked configuration, now that the bone probe shaft 110 is in a stabilized in position. The surgeon may then move the handle in a directions towards the bone until the first end of the handle abuts the surface of the bone or the surface of the plate/implant, as shown in FIG. 12E, at which point, the depth gauge member 116 can be used for measuring the depth of the hole. As shown in FIG. 12F, the surgeon may then advance the depth gauge member 116 towards hole, via the second slider 350, such that the distal end 120 of the depth gauge member shaft 118 extends from the first end of the device handle and advances into the hole, sliding over the bone probe 108. While the bone probe 108 is maintained in engagement with the bottom of the hole via the probing tip, the depth gauge member may be advanced in a direction towards the bottom of the hole until the distal end of the depth gauge member makes contact with the bottom of the hole. The bone probe essentially acts as a guide upon which the depth gauge member slide over when advancing to the bottom of the hole.

The sensor is configured to generate an electronic signal based on a distance between the first end of the body and the distal end of the depth gauge member, wherein the electronic signal is indicative of at least a depth of the hole. In particular, the sensor may include inductive or capacitive elements or assemblies configured to sense the location of the distal end of the depth gauge member relative to the first end of the device body, and, as a result, generate an electronic signal representing the distance there between. Accordingly, the sensed distance between the first end of the device handle (when abutting the bone surface) and the distal end of the depth gauge member (when abutting the bottom of the hole) is the depth of the hole.

It should be noted that the device may include logic or allow for adjustment to the sensing capabilities so as to program the sensor to account for other variables when sensing the depth of the hole. For example, in some embodiments, certain procedures require fixing a plate or implant to the bone via screws. Accordingly, the screw length must not only be sufficient to fill the hole but also long enough to account for the thickness of a plate or implant through which it passes when engaging the hole. Accordingly, in some embodiments, the sensor may be programmed so as to account for the thickness of the plate or implant and will further include that thickness in the electronic signal produced, such that the electronic signal is indicative of the total depth that a corresponding screw length will need to cover, including the depth of the hole in the bone in addition to the thickness of the plate or implant through which the screw will pass through and the screw head will engage.

Furthermore, in some instances, first end of the device handle will be directly abutting a surface of the plate or implant, as shown in FIG. 12F, which is directly abutting the surface of the bone, when the surgeon is measuring the depth. Thus, in this case, the sensor is still able to sense a distance between the first end of the device handle and the distal end of the depth gauge member, which will provide an overall depth, rather than just a depth of the hole in the bone.

FIGS. 13A-13C illustrate a series of steps for performing a procedure of probing a fully drilled hole (i.e., a hole extending entirely through a bone for receipt of a bicortical bone screw) with the bone probe 208 and further establishing purchase of the probing tip 212 of the bone probe 208 with a side of the bone adjacent to the bicortical drilled hole to secure the bone probe 208 in place and allow the depth gauge member to be used for measuring the depth of the bicortical drilled hole. It should be noted that he bone probe 208 of FIGS. 4-9 is compatible for use with either of devices 100 and 300 and may be extended and retracted, and otherwise manipulated for subsequent probing and depth measurements, therefrom in a similar manner as bone probe 108 previously described herein.

As shown in FIGS. 13A-13C, the hole is drilled entirely through the bone (i.e., bicortical drill hole), and thus a surgeon will need to not only probe the interior surface of the hole, and possible obtain neuromonitoring data (i.e., determine whether there are any nearby nerves which may be affected by placement of a screw within the hole), but further obtain an accurate measurement of the depth of the entire hole.

As shown in FIG. 13A, a surgeon may first perform examination of the drilled hole with the probing tip 214 by advancing the bone probe 208 into the drilled hole. The surgeon may simply apply slight pressure such that the base portion 220 of the probing tip 214 contacts an interior surface of the hole and, in return, provides tactile feedback of the interior surface to the surgeon. The base portion 220 is shaped so as to glide or easily slide along the interior surface, while still allowing sufficient contact to provide tactile feedback to the surgeon. The surgeon may then advance the probing tip 214 entirely through the hole, at which point, the base portion 220 will cease contact with the interior surface and the surgeon will sense (via tactile feedback) that the end of the hole has been reached (shown in FIG. 13B).

At this point, upon the surgeon extending the probing tip 214 entirely through a bicortical drilled hole, the surgeon can then establish purchase between the top portion 222 of the probing tip 214 and a portion of an opposing side of bone so as to secure the bone probe shaft 210 in place for subsequent depth measurements with the depth gauge member. For example, as shown in FIG. 13C, the surgeon may simply position the substantially planar second side 218 against the interior surface of the drilled hole and then retract (i.e., pull back) the probe shaft 210 such that the engagement surface 226 of the top portion 222 of the probing tip 214 comes into contact with a portion of the opposing side of the bone immediately adjacent to the opening of the hole. The engagement surface 226 may be a substantially abrupt edge of the probing tip 214, in which the transition between the base portion 220 and the top portion 222 is sudden (e.g., sharp corner or edge). Accordingly, as the surgeon is pulling the bone probe shaft 210 back towards the hole, the engagement surface 226 will begin to contact the bone. In some embodiments, the engagement surface 226 may include surface texturing to enhance friction between the engagement surface 226 and the portion of bone to reduce risk of slippage during bicortical depth measurements. Furthermore, groove 224 (present at the junction between the distal end 212 of the probe shaft 210 and the probing tip 214) will allow for additional flexing of the probing tip 214 relative to the remainder of the probe shaft 210 due to less material at the junction between the shaft 210 and the tip 214 at the groove 224, which will improve the purchasing or grabbing of the opposing side of the bone with the engagement surface 226 of the top portion 222 of the probing tip. Furthermore, the tapered thickness of the shaft 210, provided by the substantially planar second side 218, allows for deflection or bending of the shaft 210 on one axis, such that, if the probing tip 214 is substantially perpendicular to shaft 210, as generally shown, application of pressure upon the shaft 210 results in deflection of the probing tip 214, particularly the engagement surface 226, to become angled upward, thereby enabling a superior purchase or gripping of the outer surface of the opposing side of the bone. Upon securing the bone probe 208 in place, depth measurements may take place with the depth gauge member in a manner similar to that of bone probe 108 previously described herein.

Figure 14:
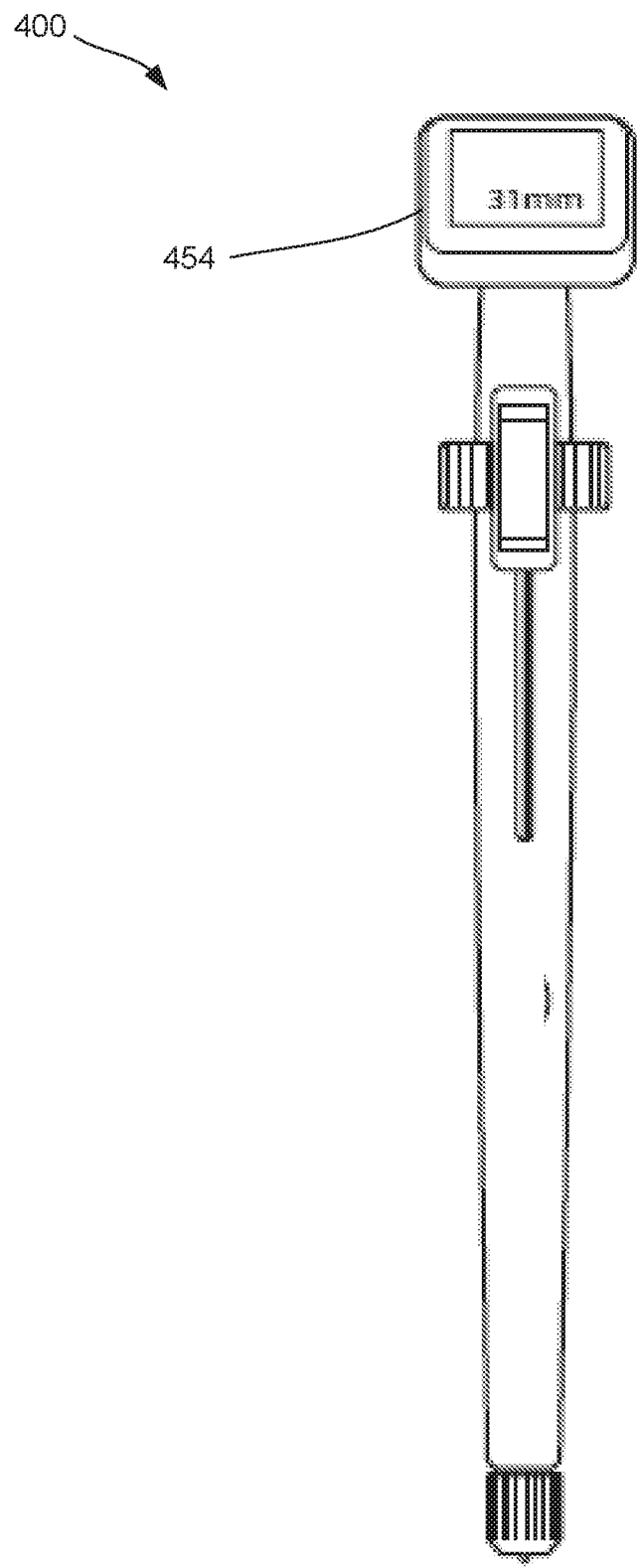
FIG. 14 is another embodiment of a medical device consistent with the present disclosure having a display for providing a digital readout of a depth measurement of the hole.

FIG. 14 is another embodiment of a medical device 400 consistent with the present disclosure having a display 454 for providing a digital readout of a depth measurement of the hole based on the electronic signal from the sensor. The display 454 may include a liquid crystal display or an LED display, for example.

Figure 15:
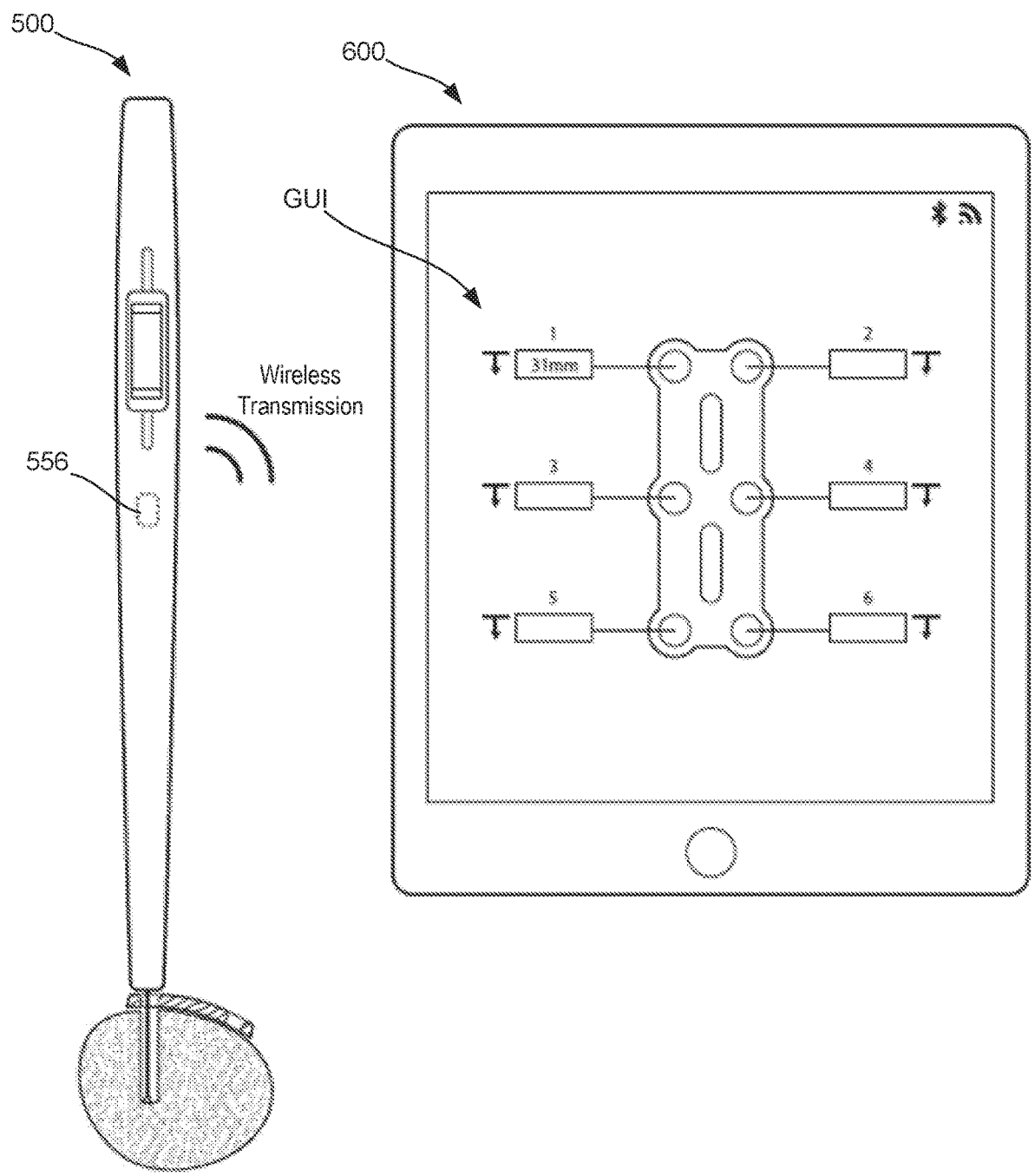
FIG. 15 is another embodiment of a medical device consistent with the present disclosure configured to wirelessly communicate with and transmit depth measurement data to a wireless computing device to record, store, and/or visually display measured depths.

FIG. 15 is another embodiment of a medical device 500 consistent with the present disclosure configured to wirelessly communicate with and transmit depth measurement data to a wireless computing device 600 over a network, to record, store, and/or visually display measured depths based on electronic signals from the sensor for determining depth of drilled holes. For example, the device 500 may include a wireless transmitter 556 configured to wireless communicate and exchange information, including the electronic signal, with a wireless display or computing device 600 for at least visually providing a depth measurement of the hole based on the electronic signal from the sensor. The separate display or computing device 600 may include, but is not limited to, a monitor or panel display, a PC, a notebook, a tablet computer, a smartphone, or other computing device configured to wirelessly communicate with the wireless transmitter 556.

The network may be any network that carries data. Non-limiting examples of suitable networks that may be used as network include WiFi wireless data communication technology, the internet, private networks, virtual private networks (VPN), public switch telephone networks (PSTN), integrated services digital networks (ISDN), digital subscriber link networks (DSL), various second generation (2G), third generation (3G), fourth generation (4G) cellular-based data communication technologies, Bluetooth radio, Near Field Communication (NFC), the most recently published versions of IEEE 802.11 transmission protocol standards, other networks capable of carrying data, and combinations thereof.

Furthermore, in some embodiments, the computing device 600 may include a specific software application that may be directed to maintaining a record of the hole measurements and/or provide an interactive user interface (GUI) in which multiple holes can be mapped to a particular plate or implant and the depth of each hole (including the thickness of the plate or implant) can be included and stored for records.

Figure 16:
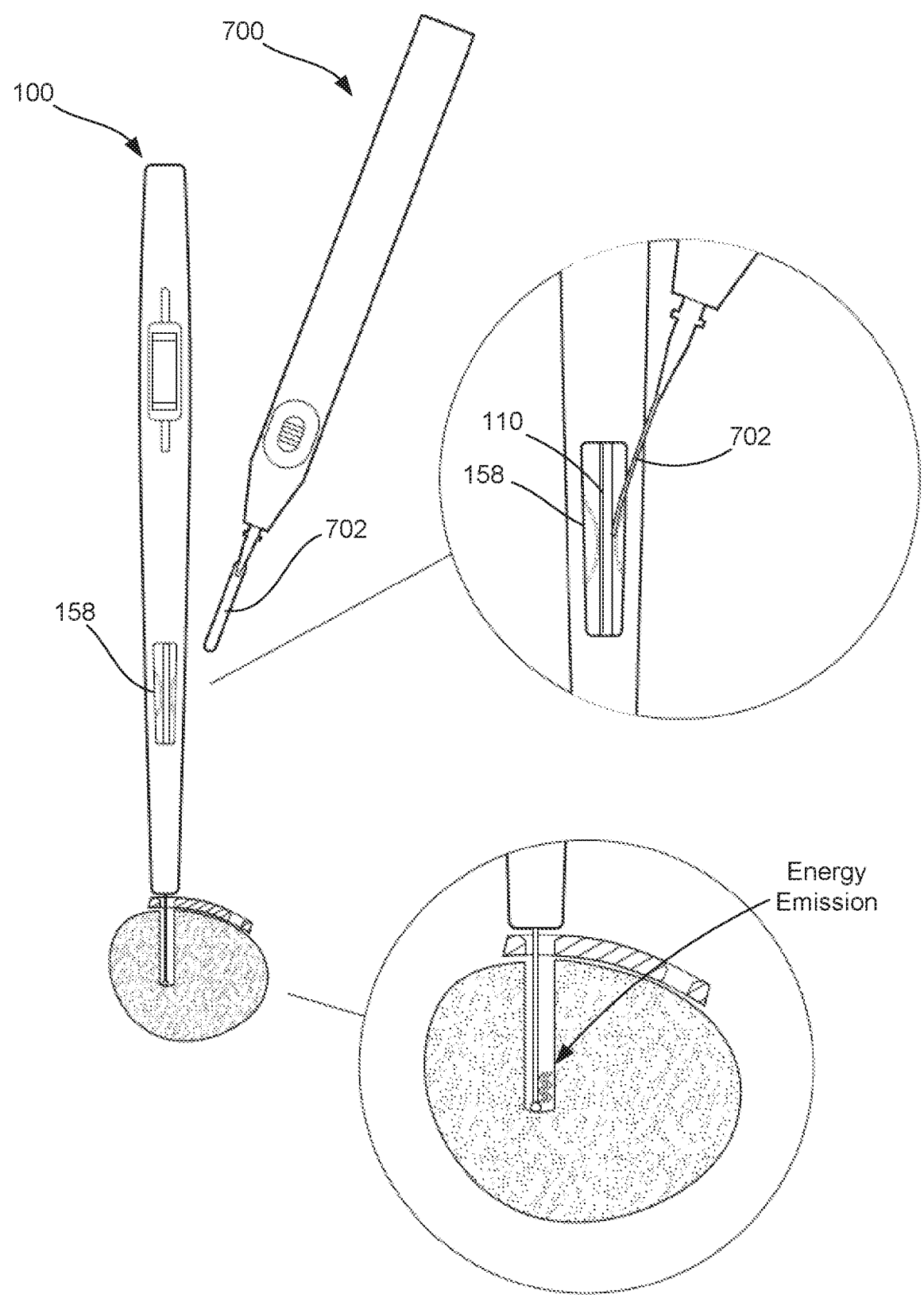
FIGS. 16 and 17 illustrate the compatibility of a medical device of the present disclosure with other medical devices so as to provide additional features, in additional bone probing and depth measurement, such as energy emission (FIG. 16) and sensing capabilities (FIG. 17)
Figure 17:
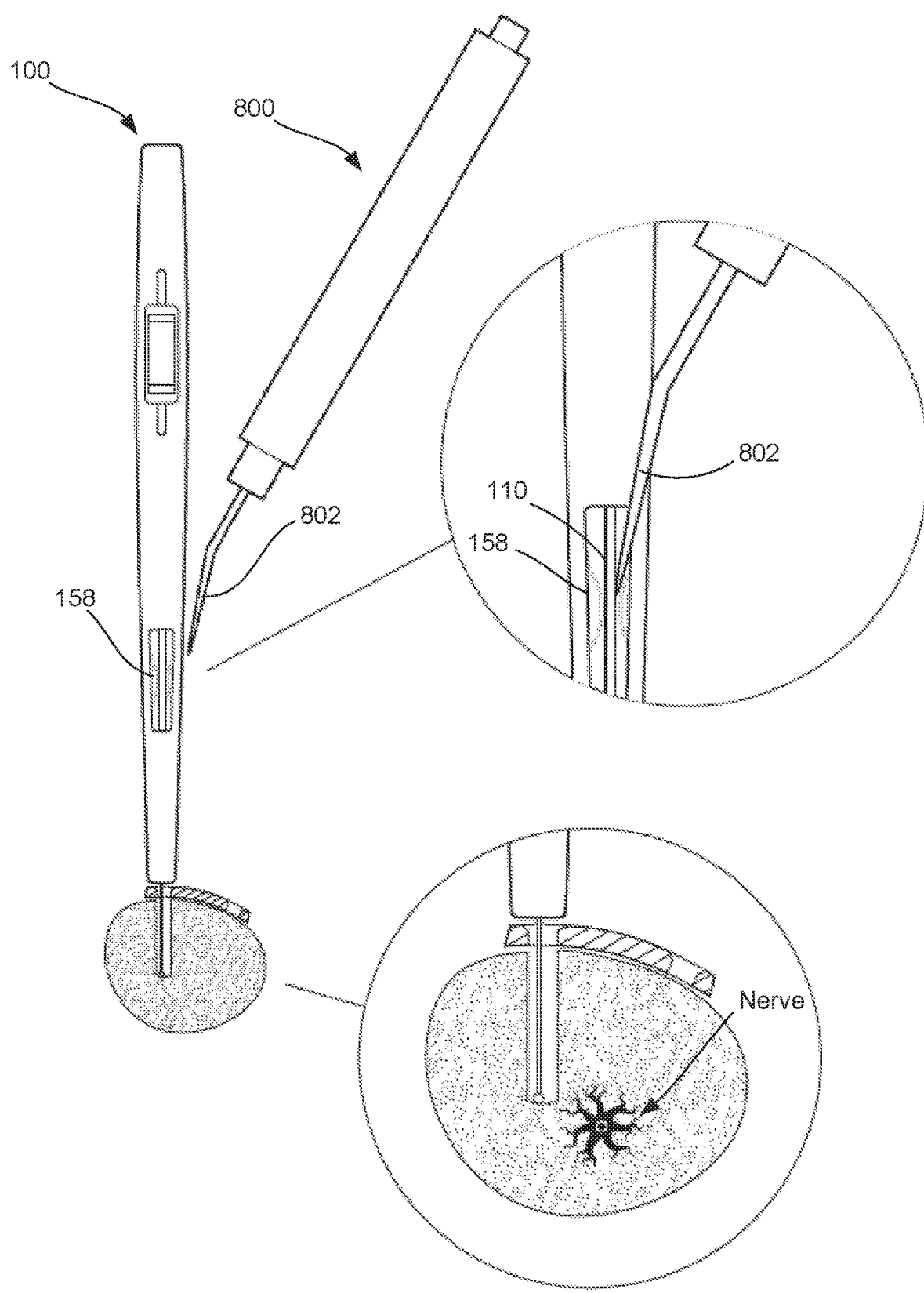

FIGS. 16 and 17 illustrate the compatibility of a medical device of the present disclosure with other medical devices so as to provide additional features, in additional bone probing and depth measurement, such as energy emission (FIG. 16) and sensing capabilities (FIG. 17). For example, in some embodiments, the bone probe shaft 110, 210 may include an electrically conductive material (e.g., a metal such as stainless steel, nitinol, or aluminum), wherein a portion of the bone probe shaft 110, 210 may be exposed, or otherwise accessible, along a portion of the device handle. In particular, the device handle may include an access region 158 that may be in the form of an aperture, window, or the like, that provides access to an interior of the handle, particularly providing access to an exposed portion of the bone probe shaft. Thus, in some embodiments, an electrical current from a separate device 700, 800 may be supplied to the bone probe shaft via the access region 158 (e.g., slide a working tip 702 of an electrocautery device 700 into the access region 158 to make contact with bone probe shaft 110, 210). Accordingly, as a result of being made from a conductive material, the bone probe shaft 110, 210 may carry the electrical current to the distal probe tip, which may then be used to deliver energy to a desired target (e.g., interior surface of hole of the bone) as a result of the electrical current applied thereto. Similarly, a separate nerve sensing/stimulation device 800 (shown in FIG. 17) may be coupled to the conductive bone probe shaft via the access region (i.e., slide a working tip 802 of the device 800 into the access region 158), such that the distal probe tip essentially acts as an extension to the nerve sensing/stimulation device and may be used to sense/stimulate nerves within the bone. The separate sensing/nerve stimulation device or system 800 may include, for example, existing capital equipment or a handheld battery-powered neuromonitoring device.

Figure 18:
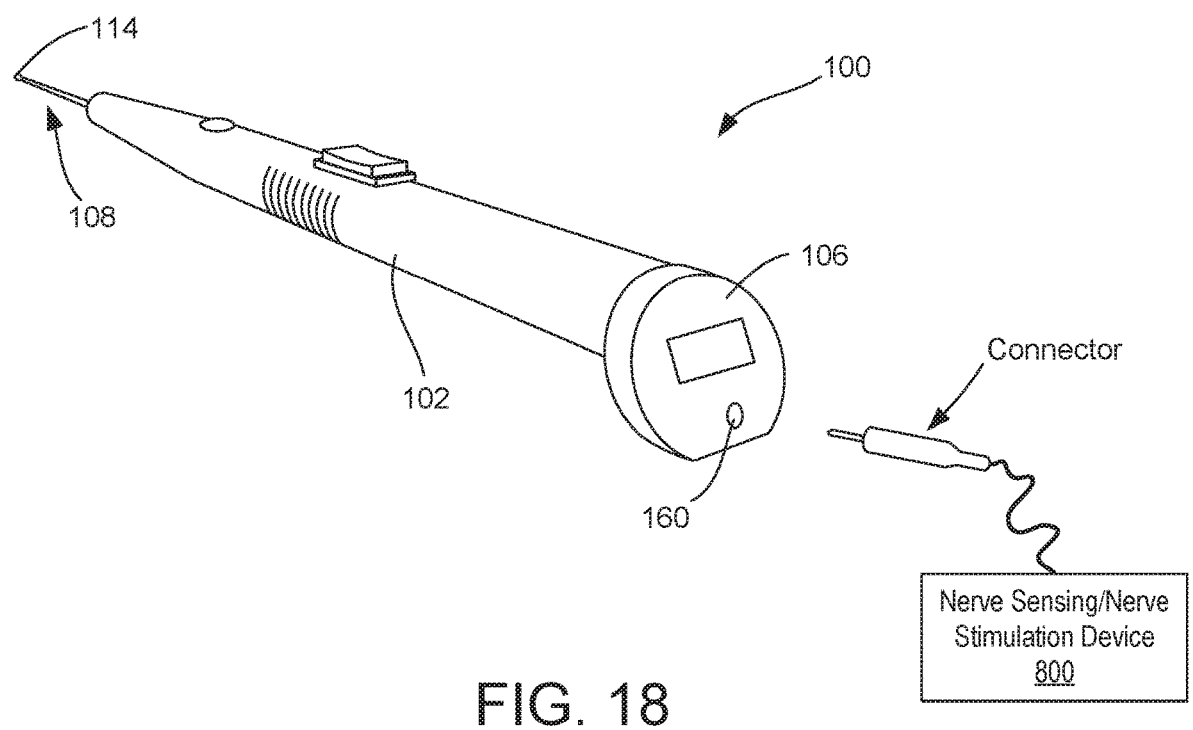
FIG. 18 is a perspective view of a medical device consistent with the present disclosure and having a neuromonitoring port configured to receive a corresponding input connector from a nerve sensing/nerve stimulation device and provide an electrical pathway to the bone probe.

FIG. 18 is a perspective view of a medical device 100 having a port 160 provided on the proximal, or second end 106, of the device body 102. The port 160 is configured to receive a corresponding input connector from a nerve sensing/nerve stimulation device 800. The port 160 (hereinafter referred to as "neuromonitoring port 160") is coupled to the bone probe shaft 110, 210 and is configured to provide an electrical pathway from the nerve sensing/nerve stimulation device 700 to the bone probe 108, 208 upon insertion of the input connector into the neuromonitoring port 160. As previously described, the bone probe shaft 110, 210 may include an electrically conductive material (e.g., a metal such as stainless steel, nitinol, or aluminum) and thus may carry an electrical signal. Thus, in some embodiments, an electrical signal from the nerve sensing/nerve stimulation device 800 may be supplied to the bone probe shaft 110, 210 via the neuromonitoring port 160. Accordingly, as a result of being made from a conductive material, the bone probe shaft 110, 210 may carry the electrical signal to the distal probe tip 114, 214, which may then be used to sense/stimulate nerves adjacent or in close proximity to the drilled hole in the bone, either when the bone probe 108, 208 is directly placed within the drilled hole or when the bone probe 108, 208 is in contact with a screw placed within the drilled hole.

Figure 19:
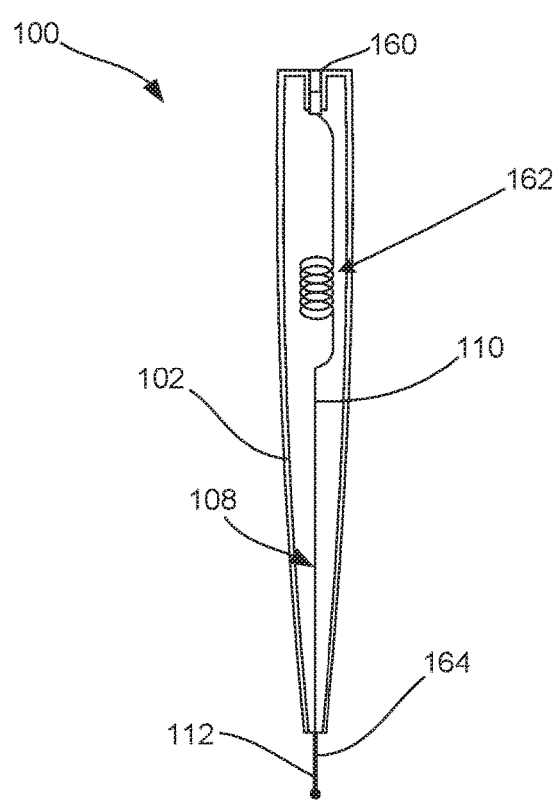
FIG. 19 is a side view, partly in section, of the medical device of FIG. 18 illustrating the configuration of the bone probe shaft to carry electrical signals to and from the nerve sensing/nerve stimulation device.

FIG. 19 is a side view, partly in section, of the medical device 100 of FIG. 18 illustrating the configuration of the bone probe shaft 110 for carrying electrical signals to and from the nerve sensing/nerve stimulation device. It should be noted that bone probe shaft 210 is also compatible with the nerve sensing/nerve stimulation device and can function in a similar manner as bone probe shaft 110 described herein. Upon insertion of the electrical connector into the neuromonitoring port 160, a pathway is provided between the nerve sensing/nerve stimulation device 700 and the bone probe 108. The bone probe shaft 108 generally includes a soft coil portion 162 configured to allow conduction of an electrical signal provided by the nerve sensing/stimulation device 800 while the shaft 110 moves between fully retracted and fully extended positions and intermediate positions there between, particularly when measuring the depth of the drilled hole 134. In some embodiments, a portion of the distal end 112 of the bone probe 108, particularly the exposed portion of the shaft 110 extendable outside of device body 102 may include an insulating material 164, while the distal probing tip 114 is free of insulating material.

Figure 20A:
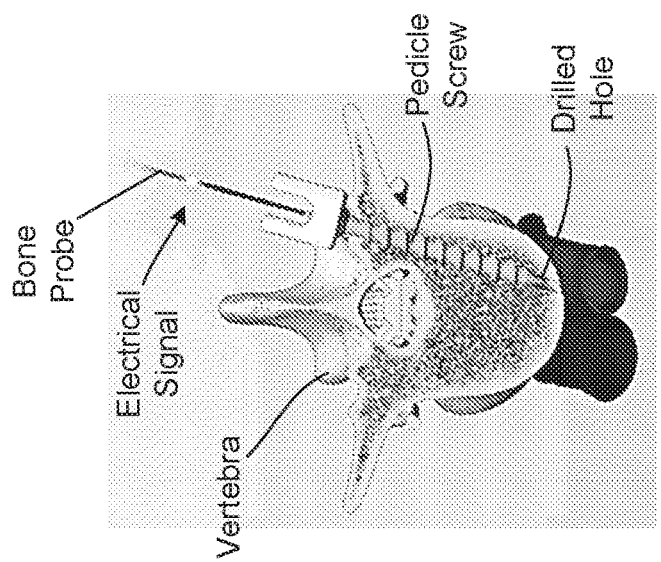
FIGS. 20A, 20B, 20C illustrate the transmission of a signal from bone probe to a screw positioned within a hole in a vertebra for neuromonitoring capabilities.
Figure 20B:
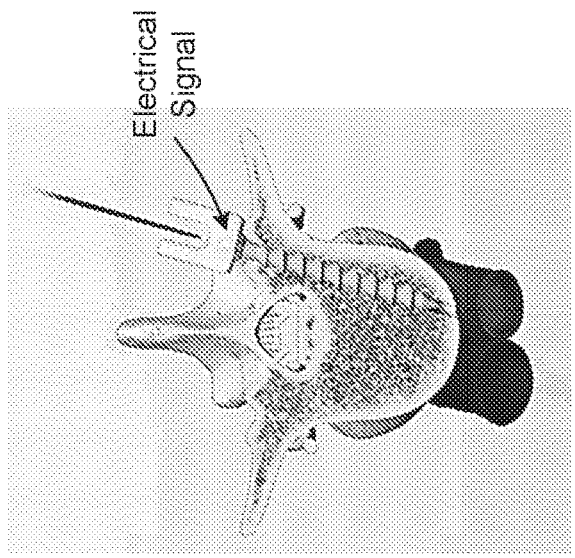
Figure 20C:
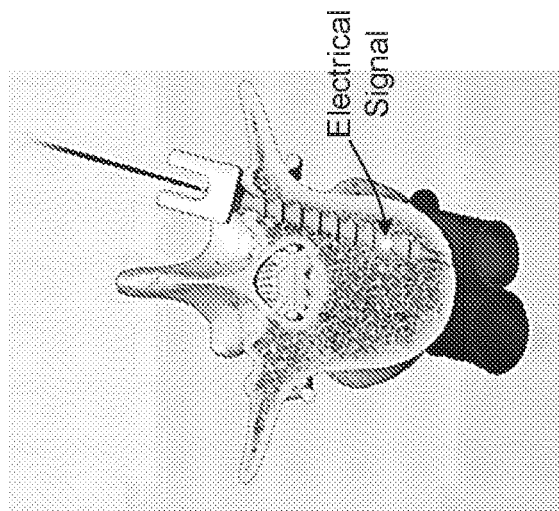

FIGS. 20A, 20B, and 20C illustrate the transmission of a signal from bone probe 108 to a screw positioned within a hole in a vertebra for neuromonitoring capabilities. As shown in FIG. 20A, upon coupling the nerve sensing/nerve stimulation device 700 to the medical device 100 (e.g., inserting the electrical connector into the neuromonitoring port 160), a surgeon can begin a neuromonitoring procedure to determine whether there are any critical neurological structures adjacent to or within an unsafe proximity to the drilled hole and screw. In particular, a surgeon can perform neuromonitoring procedure by placing the bone probe 108 directly within the drilled hole prior to screw placement, in which the distal probing tip 114 can be placed in direct contact with the interior of the hole and transmit the electrical signal from the nerve sensing/nerve stimulation device 800 to the bone tissue and will subsequently receive a response signal to then be carried back to the nerve sensing/nerve stimulation device 700 for processing. In another method, as shown in FIGS. 20A, 20B, and 20C, the surgeon is performing the neuromonitoring procedure once the screw is already in place (e.g., already fitted within the drilled hole) by placing the distal probing tip 114 in direct contact with the screw, which, in turn, will act as a conduit and carry electrical signals to and from the distal probing tip 114 and the nerve sensing/nerve stimulation device 900.

Accordingly, the medical device consistent with the present disclosure is a three-in-one single use device designed to more accurately and safely measure the screw hole pathway. For example, the probing tip of the bone probe provides a user (e.g., surgeon) with superior tactile feedback to assist the surgeon in confirming a safe pathway within the bone. The electronic measurement/digital sensing is designed to provide more accurate depth measurement for the screw pathway. The neuromonitoring feature is used to stimulate the pathway and/or screw, ensuring the screw is safely positioned away from any critical neurological structures. Overall, the medical device of the present disclosure is a faster, safer, more accurate and user-friendly solution for surgeons when placing bone screws, particularly pedicle screws during spinal fusion surgery, thereby minimizing spine surgery complications and reducing overall healthcare costs.

Figure 21:
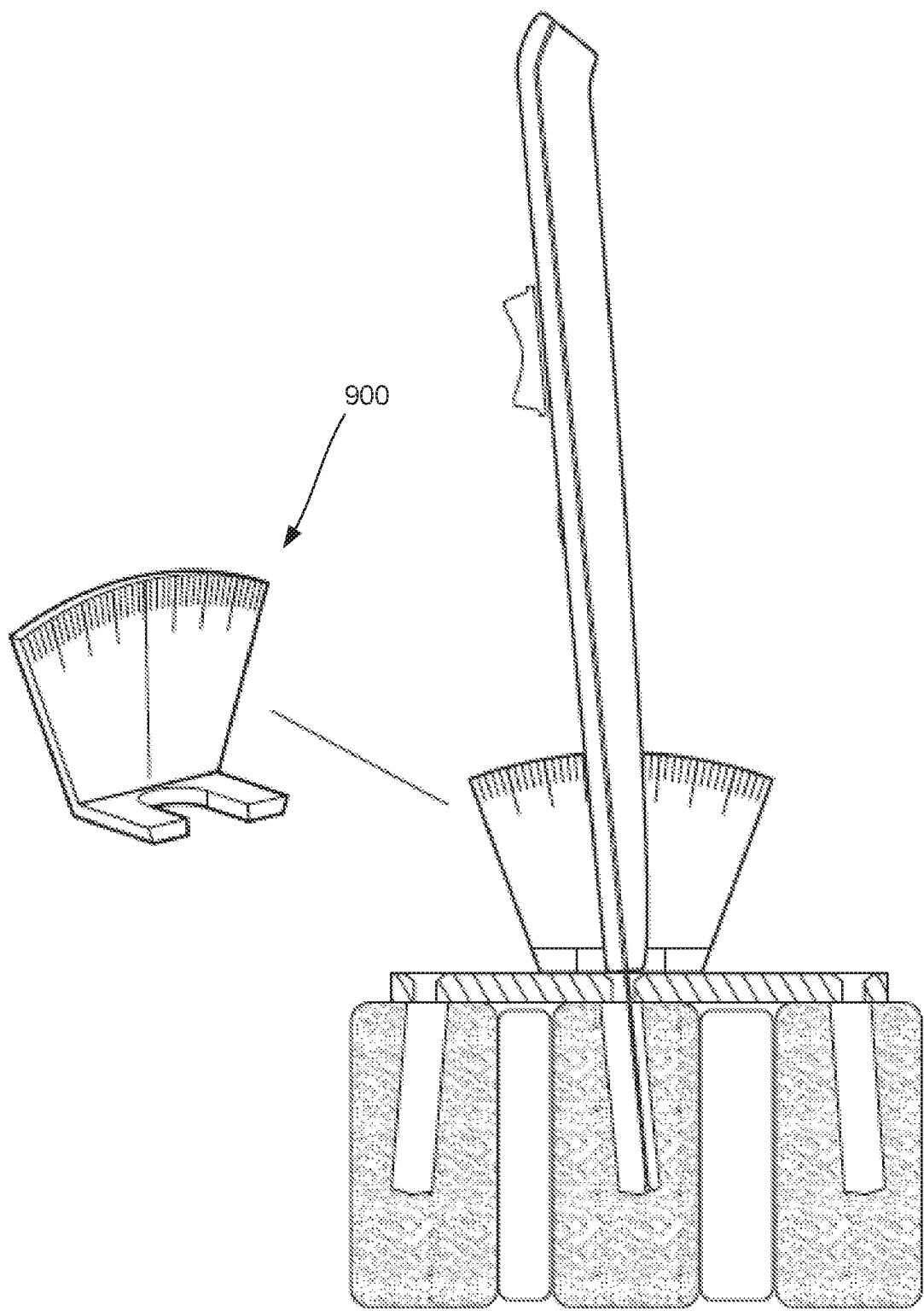
FIG. 21 illustrates an angle guide for use with the medical device of the present disclosure.

FIG. 21 illustrates an angle guide 900 for use with the medical device of the present disclosure. In some instances, holes may be drilled into bone at an angle. Accordingly, the angle guide may be useful in providing a surgeon with a visual guide as to the correct angle at which to position the device when attempting to examine the hole and further locate the bottom of the hole to carry out the depth measurements.

Figure 22:
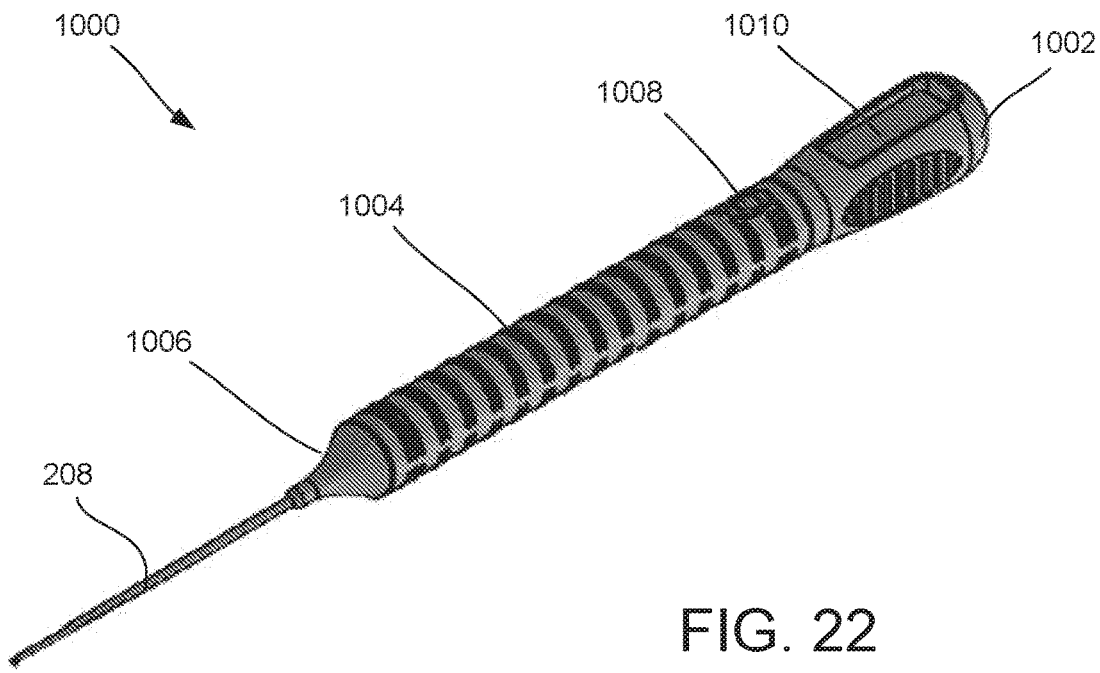
FIG. 22 is a perspective view of another embodiment of a medical device consistent with the present disclosure.
Figure 23:
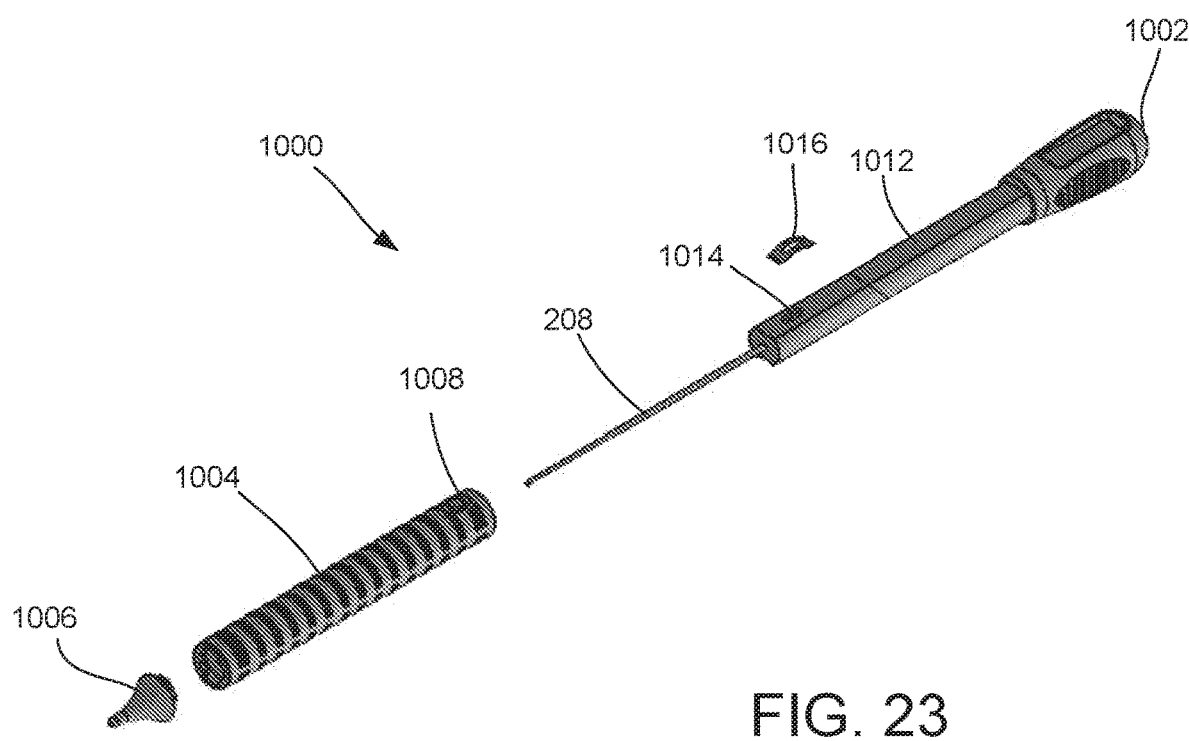
FIG. 23 is a perspective, exploded view of the medical device of FIG. 22.

FIG. 22 is a perspective view of another embodiment of a medical device 1000 consistent with the present disclosure. FIG. 23 is a perspective, exploded view of the medical device 1000. The device 1000 is configured to provide a faster and more accurate measure of depth. In particular, the device 1000 includes a combination of a bone probe allowing for physical examination of a hole drilled in a bone and a depth gauge member for determining a depth of the hole and providing a digital measurement of the depth. The device 1000 generally includes a handle 1002 which includes a bone probe fixed thereto, a depth gauge cylinder 1004 slidably mounted over a portion of the handle 1002 and configured to slide along a length thereof, and a tip member 1006 releasably coupled to a distal end of the depth gauge cylinder 1004. As illustrated, the bone probe may generally include the bone probe 208 previously described herein with respect to at least FIGS. 4-9. The device 1000 further includes a least a user-operated activation mechanism 1008 (which may be in the form of a button or other actuatable input mechanism) which may activate and deactivate the depth measurement function of the device 1000, as well as other functions. As illustrated, the device 1000 further includes a display 1010 provided on the handle 1002 configured to visually provide a digital readout of a depth measurement of a hole in bone.

As shown, the depth gauge cylinder 1004 includes a hollow body including a lumen in which at least a portion of the handle 1002 and the bone probe 208 are received. In particular, the handle 1002 may generally include an elongate body 1012 extending from a proximal grip portion of the handle 1002. The depth gauge cylinder 1004 is operable to slide along a longitudinal axis of the handle body 1012 from an initial, default position (most-proximal position relative to the grip portion of the handle 1002), as shown in FIG. 22, to a most-distal position (relative to the grip portion of the handle 1002) and a plurality of positions therebetween. As further illustrated, the depth gauge cylinder 1004 comprises a one-piece, unitary construction. The tip member 1006 further includes a one-piece, unitary construction. Accordingly, the depth gauge cylinder 1004 and tip member 1006 provide a much more rigid and durable design in comparison to currently available depth measurement devices which rely on a two-piece construction. In particular, the one-piece cylindrical body of the depth gauge cylinder and tip member obviates the problem that current devices face, notably the splitting of the two-piece handles when an associated bone probe is pivoted within the hole and applies pressure to the handle.

The tip member 1006 is releasably coupled to a distal end of the depth gauge cylinder 1004, which may include a threaded engagement type coupling (i.e., the tip member 1006 can be screwed onto the distal end of the depth gauge cylinder 1004), a snap-fit coupling, a press-fit coupling, or the like. Once coupled to the depth gauge cylinder 1004, the tip member 1006 is operable to correspondingly slide with the depth gauge cylinder 1004. The tip member 1006 further includes an opening through which at least the bone probe 208 is received and travels during movement of the tip member 1006 and depth gauge cylinder 1004. The tip member 1006 further comprises a distal end including a profile corresponding to an opening in a bone plate through which a screw is to be received, as will be described in greater detail herein. In particular, as described in greater detail herein, tip member may be considered universal in that the profile may allow for the tip member 1006 to fit most shapes, sizes, and geometries of screw sockets and bone plate openings with precision and accuracy. It should be noted that the distal end of the depth gauge cylinder 1004 is operable to receive and releasably retain one of a plurality of interchangeable tip members. As such, the tip member may be swappable with any number of tip members, each having a different size, shape, geometry, profile, or the like depending on the specific implant or bone plate to be used. Accordingly, only the tip member need be changed, while the remaining device is sufficient for the intended procedure.

The device 1000 further includes a sensor configured to generate an electronic signal indicative of a depth of the hole, wherein the electronic signal varies in relation to distance traveled by the depth gauge cylinder 1004 relative to the handle 1002 and bone probe 208. In particular, the sensor may include inductive or capacitive elements or assemblies configured to sense the location of a distal end of the depth gauge cylinder 1004, for example, relative to a specific point along the handle body 1012, and, as a result, generate an electronic signal representing the distance therebetween as a result of movement (i.e., sliding) of the depth gauge cylinder 1004. The sensor is in communication with depth gauge electronics and/or circuitry provided on a printed circuit board (PCB) (not shown) which may be provided within the depth gauge cylinder 1004. For example, the inductive or capacitive elements may include resistive stripes within the depth gauge cylinder 1004, while a copper brush spring 1016 may be provided along a portion of the handle body 112 (retained in place via a protrusion 114). The spring 1016 may provide some form of friction with the depth gauge cylinder 1004.

Figure 24:
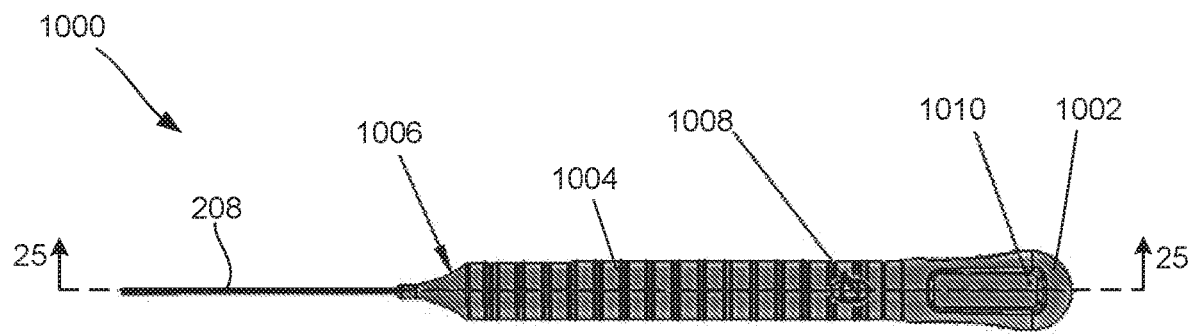
FIG. 24 is a top view of the medical device of FIG. 22 illustrating the depth gauge cylinder in the initial, default position relative to the handle and bone probe.
Figure 25:
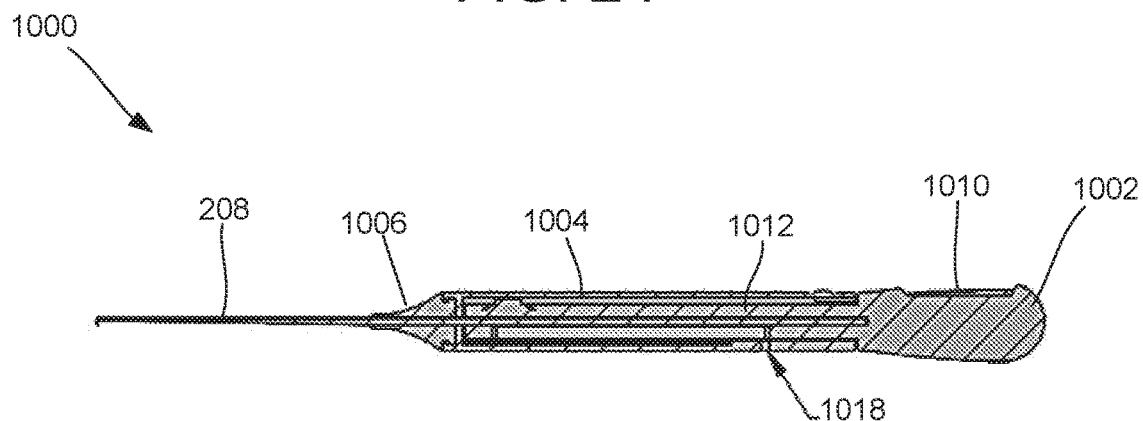
FIG. 25 is a cross-sectional view of the medical device taken along lines 25-25 of FIG. 24.
Figure 26:
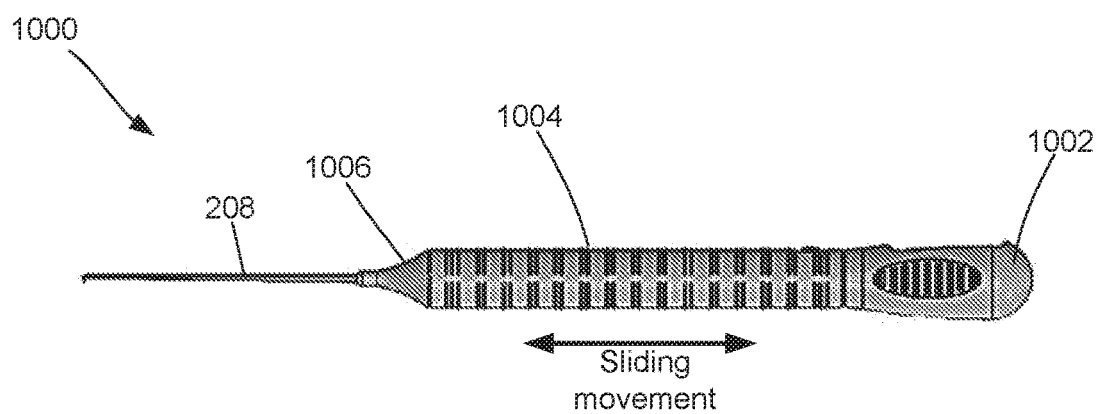
FIG. 26 is a side view of the medical device of FIG. 22.

FIG. 24 is a top view of the medical device 1000 illustrating the depth gauge cylinder 1004 in the initial, default position relative to the handle 1002 and bone probe 208. FIG. 25 is a cross-sectional view of the medical device 1000 taken along lines 25-25 of FIG. 24. FIG. 26 is a side view of the medical device of FIG. 22. As illustrated in at least FIG. 25, a dowel pin 1018 may be provided extending through a portion of the depth gauge cylinder 1004 and into engagement with a portion of the handle body 1012 to assist in retaining the depth gauge cylinder 1004 and handle body 1012 to one another (i.e., preventing the depth gauge cylinder 1004 from completely sliding off of the handle body 1012 when moving towards the bone probe tip.

Figure 27:
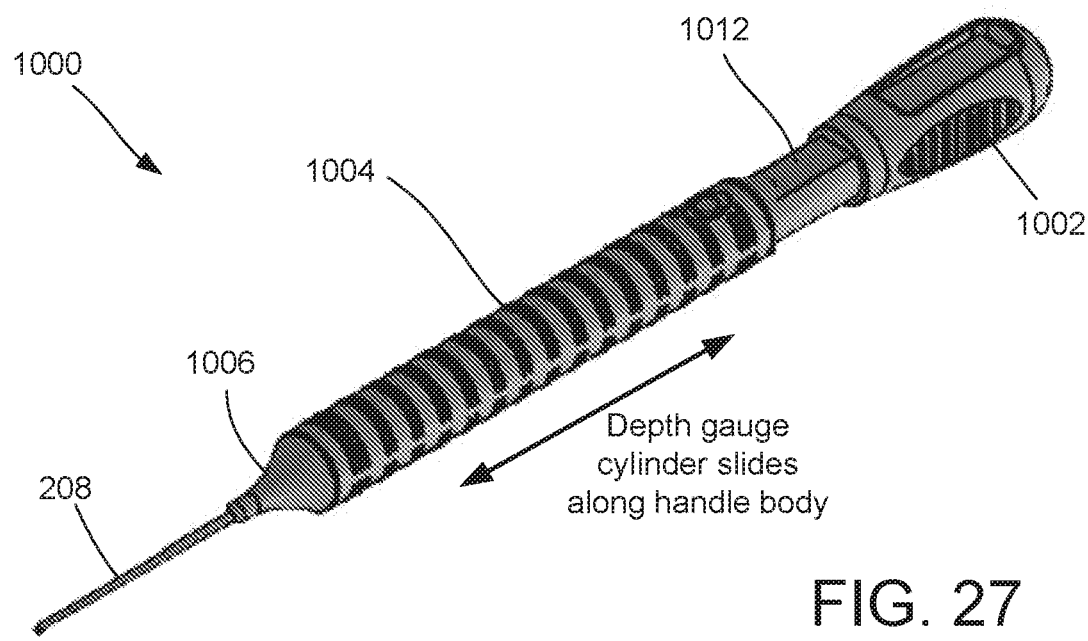
FIG. 27 is a perspective view of the medical device of FIG. 22 illustrating movement of the depth gauge cylinder relative to the handle and bone probe.

FIG. 27 is a perspective view of the medical device 1000 illustrating movement of the depth gauge cylinder 1004 relative to the handle 1002 and bone probe 208. As will be described in greater detail herein, the sensor is configured to generate an electronic signal based on the distance that the depth gauge cylinder 1004 travels relative to the handle 1002 and bone probe 208, wherein the electronic signal is indicative of at least a depth of the hole. In particular, the sensor may include inductive or capacitive elements or assemblies configured to sense the location of a distal end of the depth gauge cylinder 1004, for example, relative to a specific point along the handle body 112, and, as a result, generate an electronic signal representing the distance therebetween as a result of movement (i.e., sliding) of the depth gauge cylinder 1004. For example, the depth gauge cylinder may generally slide relative to the handle and bone probe between a most-proximal position and a most-distal position and a plurality of positions therebetween. As such, the depth gauge cylinder may be in the most-proximal position when in the default, initial position when depth measurement has not yet begun and, upon traveling a distance from the initial, default position (i.e., the most-proximal position), the traveled distance is then used to determine the depth of a hole having undergone the depth measurement with the device 1000, as will be described in greater detail herein.

Figure 28:
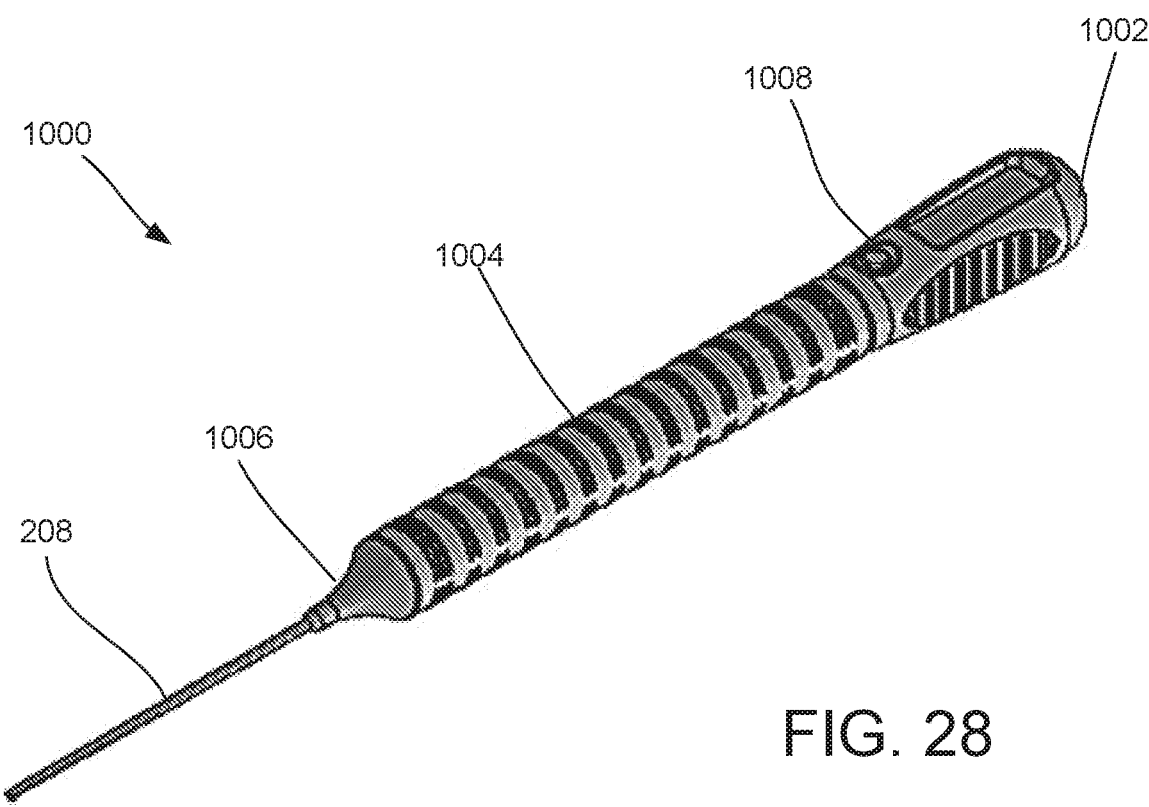
FIG. 28 is a perspective view of another embodiment of the medical device of FIG. 22 illustrating the user-operated control mechanism provided on the handle.

FIG. 28 is a perspective view of another embodiment of the medical device 1000 of FIG. 22 illustrating the user-operated control mechanism 1008 provided on the handle 1002 as opposed to the depth gauge cylinder 1004.

Figure 29A:
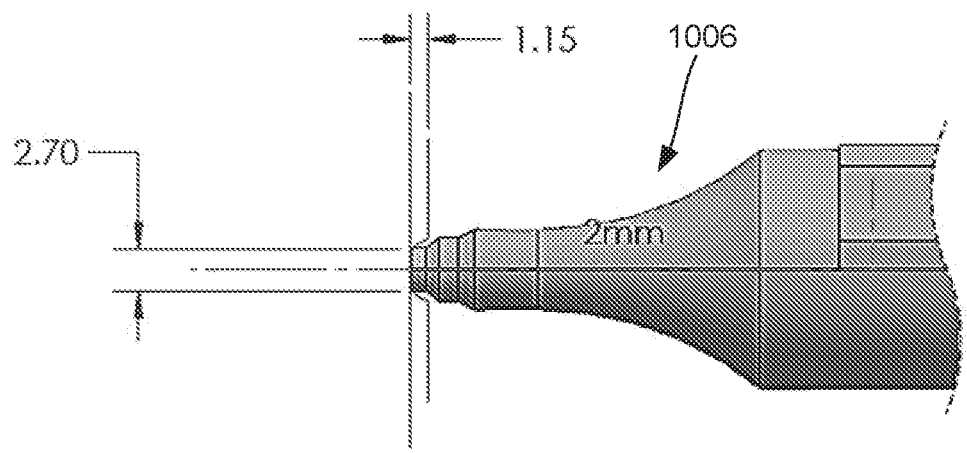
FIGS. 29A, 29B, and 29C are enlarged side views of the tip member illustrating various dimensions of the stepped profile.
Figure 29B:
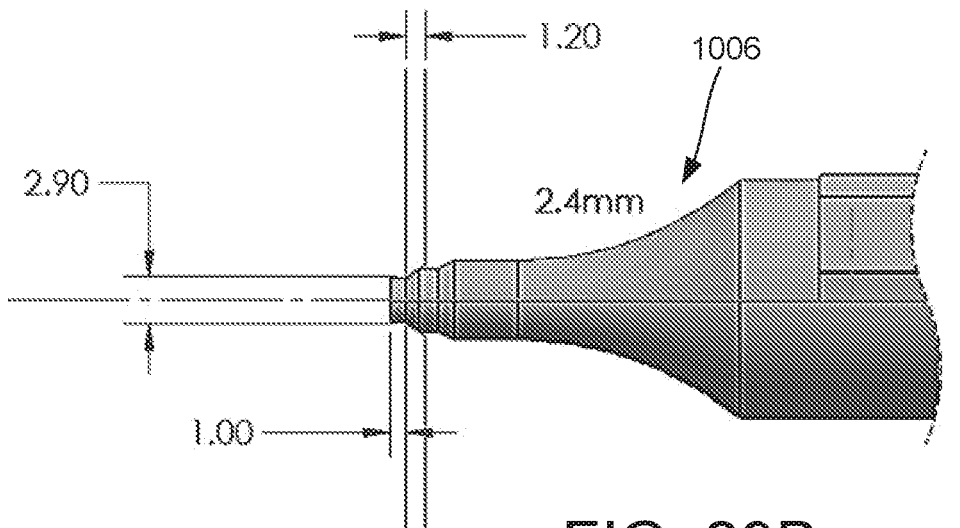
Figure 29C:
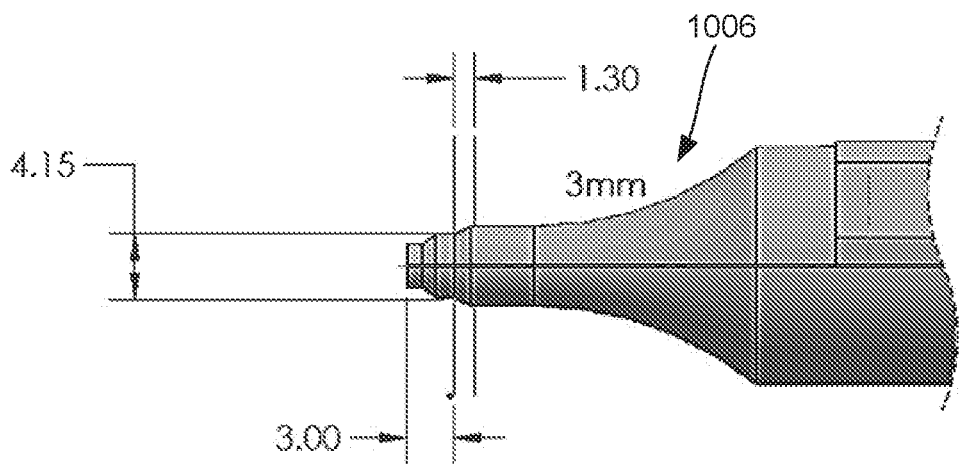

FIGS. 29A, 29B, and 29C are enlarged side views of the tip member 1006 illustrating various dimensions of the stepped profile. As previously described, the tip member 1006 includes a distal end including a profile corresponding to an opening in a bone plate through which a screw is to be received. More specifically, the tip member 1006 of the present disclosure is particularly useful in procedures in which a depth measurement is to be obtained with a bone plate in place (i.e., positioned where it would be mounted). As generally understood, it is preferable to countersink a screw when performing a bone implant fixation procedure so as to avoid any potential complications as a result of a screw head extending from a surface of bone or a bone plate. There are known generally geometries of a countersink in a bone plate hole (for receiving the screw), which include at least a mini, small, and large fragment, wherein the mini-frag is the most common. The profile of the distal end of the tip member 1006 comprises a stepped profile including multiple distinct and separate stepped portions, wherein each stepped portion has a different diameter (as illustrated in FIGS. 29A, 29B, and 29C) and tapers in diameter from a proximal position on the tip member towards a distal position of the tip member. Each of the separate stepped portions has a respective shape and/or diameter that corresponds to shapes and/or diameter of common countersink sizes provided in bone plates. Accordingly, the tip member 1006 may be considered universal in that the profile may allow for the tip member 1006 to fit most shapes, sizes, and geometries of screw sockets and bone plate openings with precision and accuracy. For example, the diameter at each stepped portion may correspond to a diameter of one of the typical geometries of the countersink (e.g., first diameter corresponds to large frag, second diameter corresponds to small frag, third diameter corresponds to mini-frag, etc.).

Figure 30:
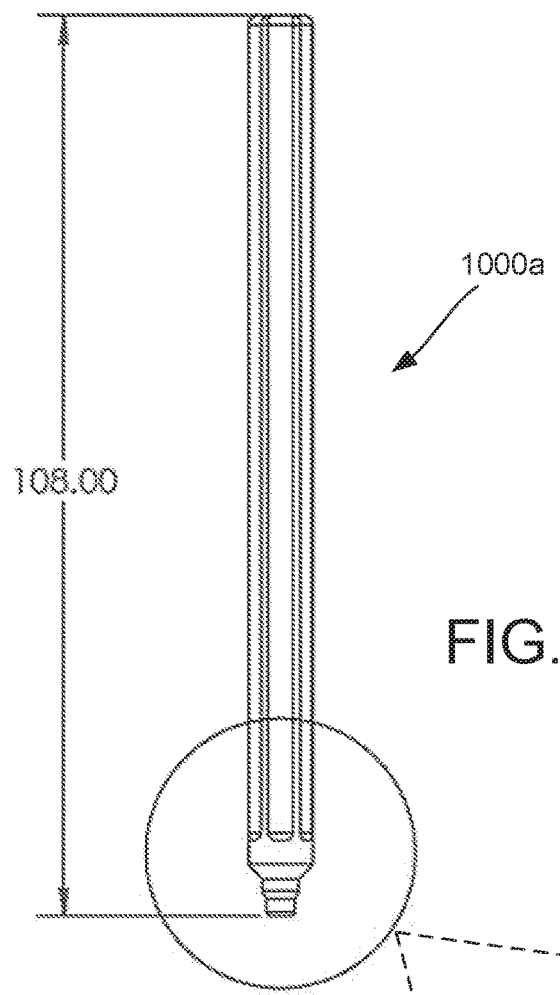
FIG. 30 is a side view of another embodiment of a medical device of FIG. 22 including a single body construction and FIG. 31 is an enlarged side view of the tip member.
Figure 31:
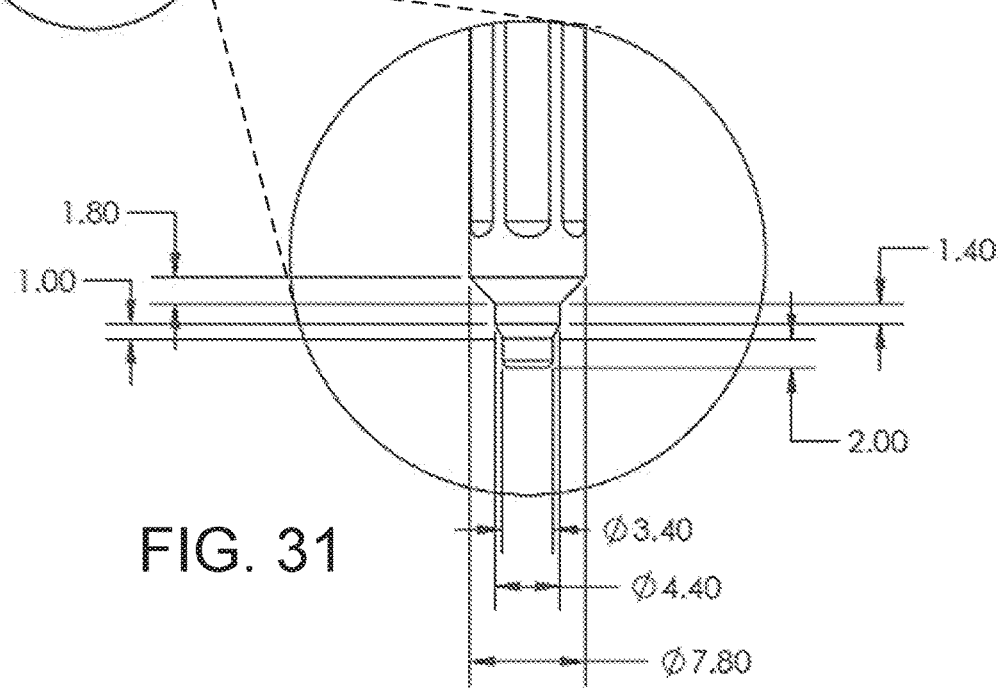

FIG. 30 is a side view of another embodiment of a medical device 1000a including a single body construction and FIG. 31 is an enlarged side view of the tip member 1006, illustrating various dimensions of the tip member profile.

Figure 32:
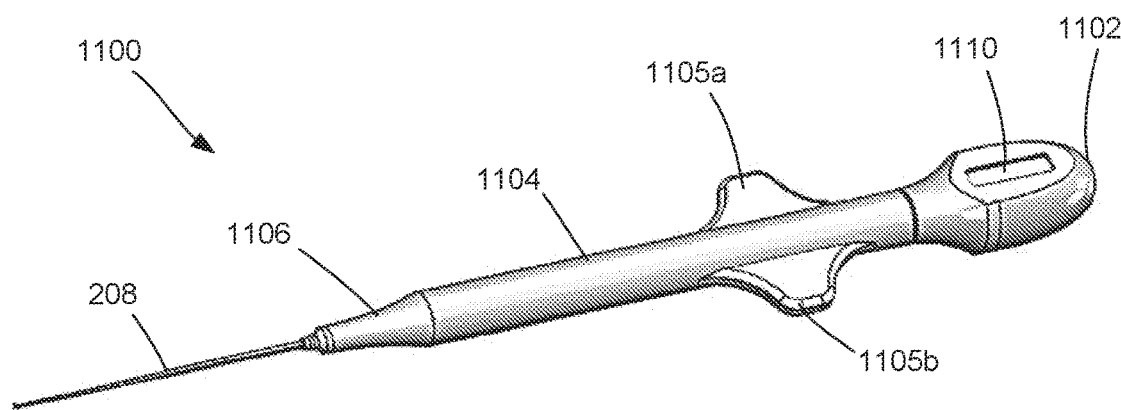
FIGS. 32 and 33 are perspective views of another medical device consistent with the present disclosure illustrating custom grip portions on portions thereof.
Figure 33:
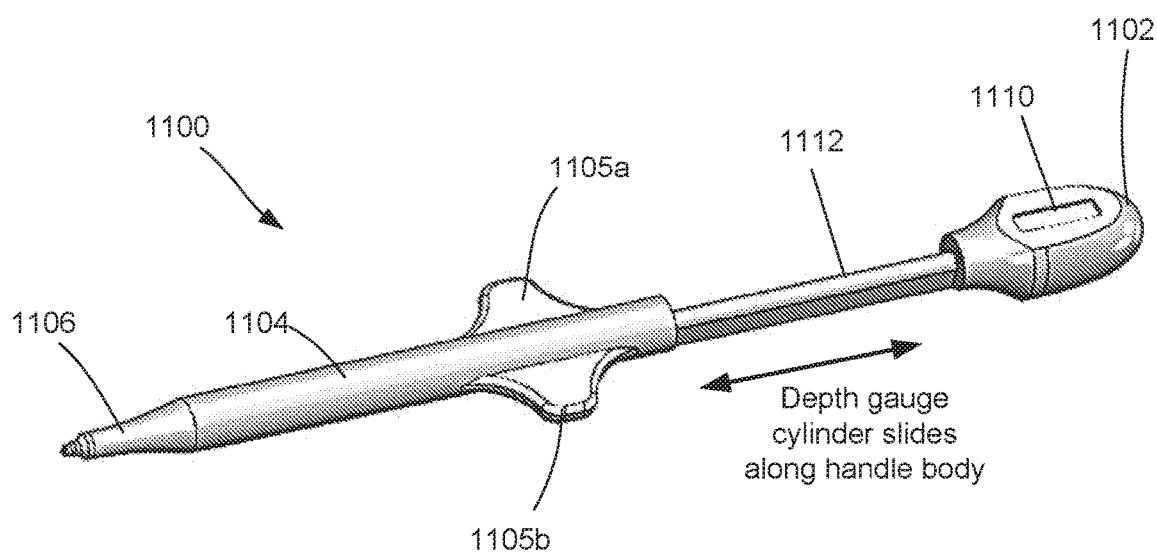

FIGS. 32 and 33 are perspective views of another medical device 1100 consistent with the present disclosure illustrating custom grip portions on portions thereof. In particular, the medical device 1100 is similar in features as medical device 1000, thus like features comprise like reference numerals. For example, medical device 1100 includes a handle 1102 which includes a bone probe 208 fixed thereto, a depth gauge cylinder 1104 slidably mounted over a portion of the handle 1102, specifically a handle body 1112, and configured to slide along a length thereof, and a tip member 1106 releasably coupled to a distal end of the depth gauge cylinder 1104. The device 1100 further includes a display 1110 provided on the handle 1102 configured to visually provide a digital readout of a depth measurement of a hole in bone. The device 1100 further includes grip portions 1105a, 1105b provided on the depth gauge cylinder 1104 which may provide improved grip for the operator during a procedure, notably during depth measuring procedures.

Figure 34:
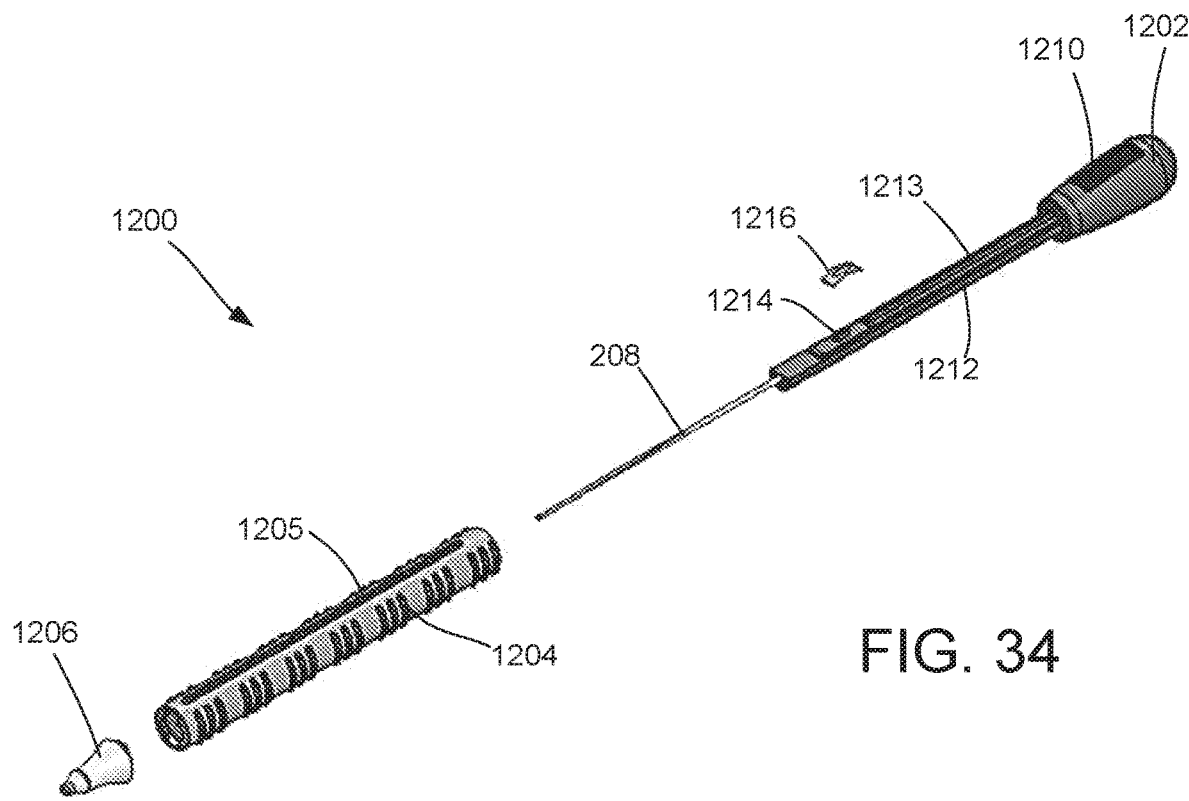
FIG. 34 is a perspective, exploded view of another embodiment of a medical device consistent with the present disclosure.
Figure 35:
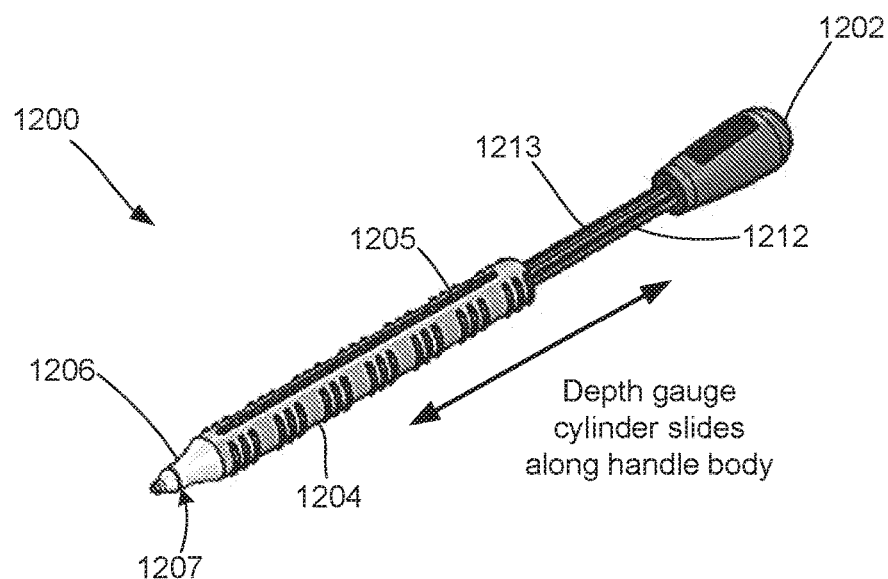
FIG. 35 is a perspective view of the medical device of FIG. 34 in an assembled state and illustrating movement of the depth gauge cylinder relative to the handle and bone probe.

FIG. 34 is a perspective, exploded view of another embodiment of a medical device 1200 consistent with the present disclosure. FIG. 35 is a perspective view of the medical device 1200 in an assembled state. The medical device 1100 is similar in features as medical device 1000, thus like features comprise like reference numerals. For example, medical device 1200 includes a handle 1202 which includes a bone probe 208 fixed thereto, a depth gauge cylinder 1204 slidably mounted over a portion of the handle 1202, specifically a handle body 1212, and configured to slide along a length thereof, and a tip member 1206 releasably coupled to a distal end of the depth gauge cylinder 1204. The tip member 1206 may further include radiopaque and/or echogenic markings, and, as such, may be viewed under various medical imaging procedures, including, but not limited to, fluoroscopy, direct visualization, and ultrasound (e.g., endoscopic ultrasound). For example, as illustrated, the tip member 1206 may include a radiopaque ring 1207 proximate the distal end thereof.

The device 1200 further includes a display 1210 provided on the handle 1202 configured to visually provide a digital readout of a depth measurement of a hole in bone. As illustrated, the depth gauge cylinder 1204 may generally slide along a track 1213 or rail assembly defined along the handle body 1212 generally corresponding to a portion 1205 of the depth gauge cylinder 1204. The depth gauge cylinder 1204 may further include an exterior surface comprising a plurality of grip portions defined thereon. The grip portions may either be protrusions or depressions either formed in the body of the depth gauge member 1204 or comprised of a separate material.

Figure 36:
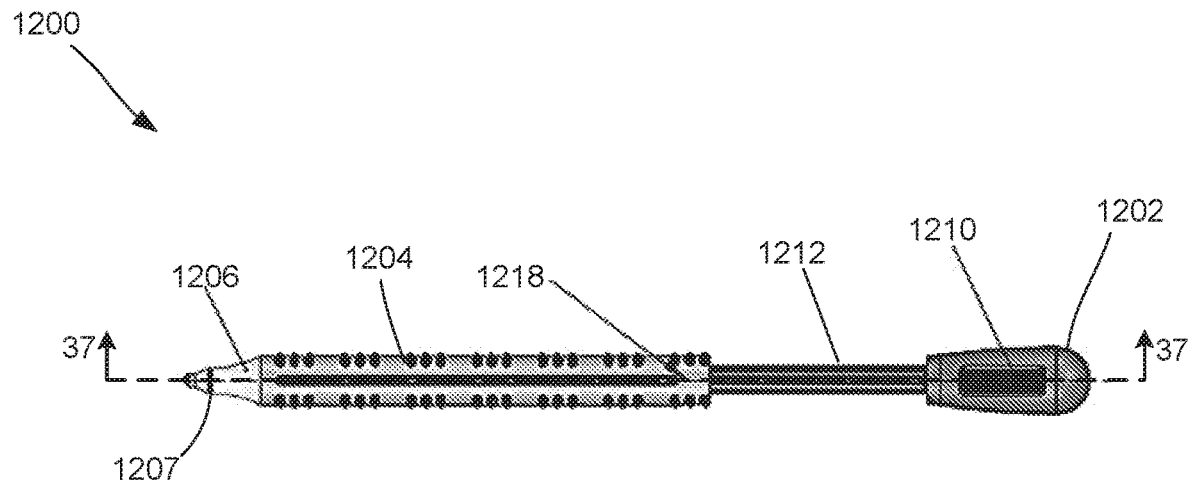
FIG. 36 is a top view of the medical device of FIG. 34 illustrating the depth gauge cylinder in a distal-most position relative to the handle and bone probe.
Figure 37:
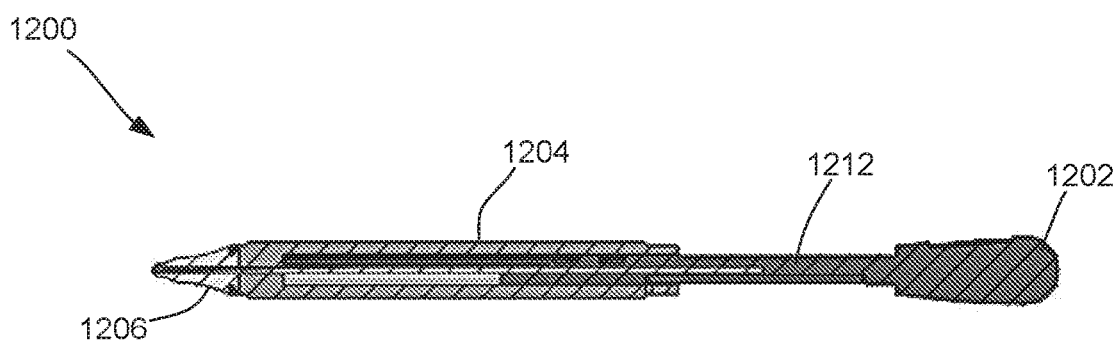
FIG. 37 is a cross-sectional view of the medical device taken along lines 37-37 of FIG. 36.
Figure 38:
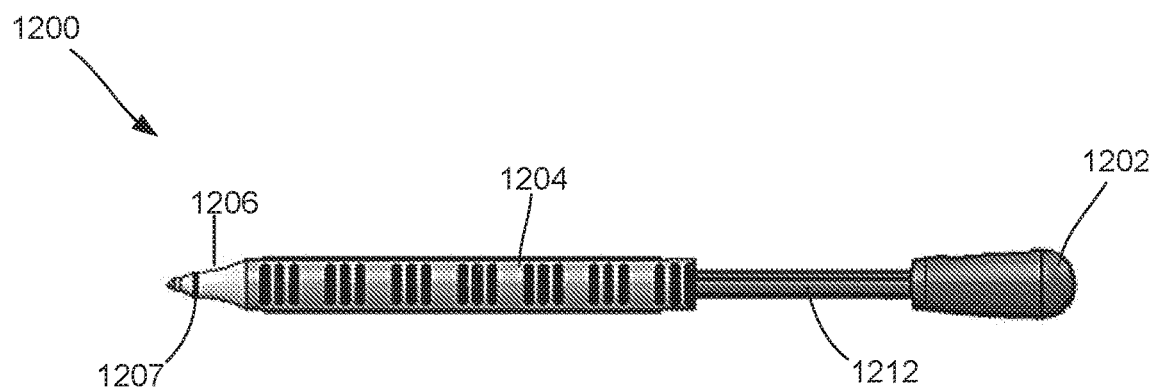
FIG. 38 is a side view of the medical device of FIG. 34.

FIG. 36 is a top view of the medical device 1200 illustrating the depth gauge cylinder 1204 in a distal-most position relative to the handle 1202 and bone probe 208. FIG. 37 is a cross-sectional view of the medical device 1200 taken along lines 37-37 of FIG. 36. FIG. 38 is a side view of the medical device 1200. As illustrated in at least FIG. 25, a set screw 1218 may be provided extending through a portion of the depth gauge cylinder 1204 and into engagement with a portion of the handle body 1212 to assist in retaining the depth gauge cylinder 1204 and handle body 1212 to one another (i.e., preventing the depth gauge cylinder 1204 from completely sliding off of the handle body 1212 when moving towards the bone probe tip.

Figure 39:
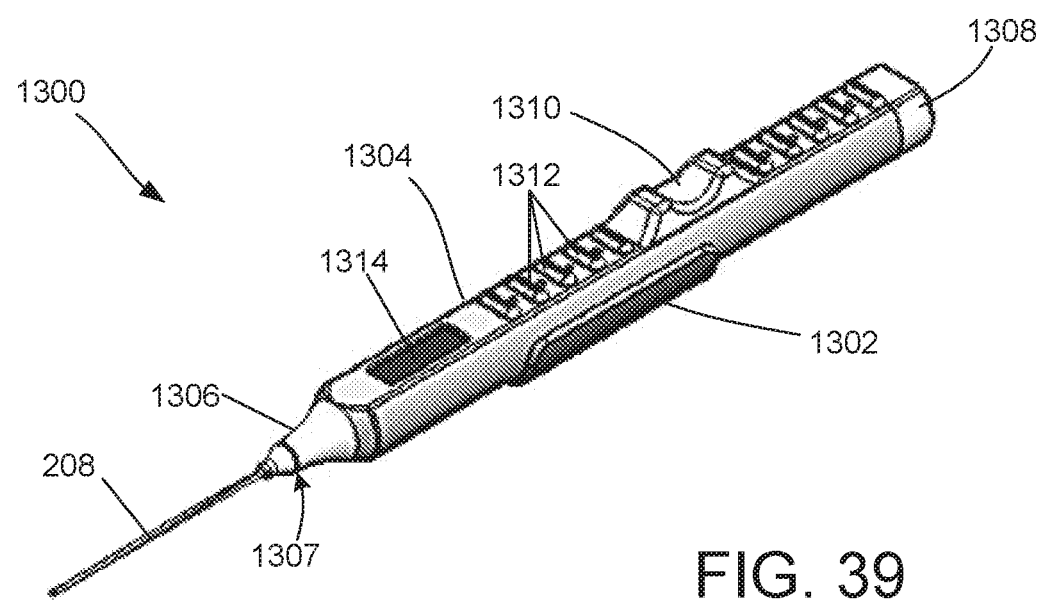
FIG. 39 is a perspective view of another embodiment of a medical device consistent with the present disclosure.
Figure 40:
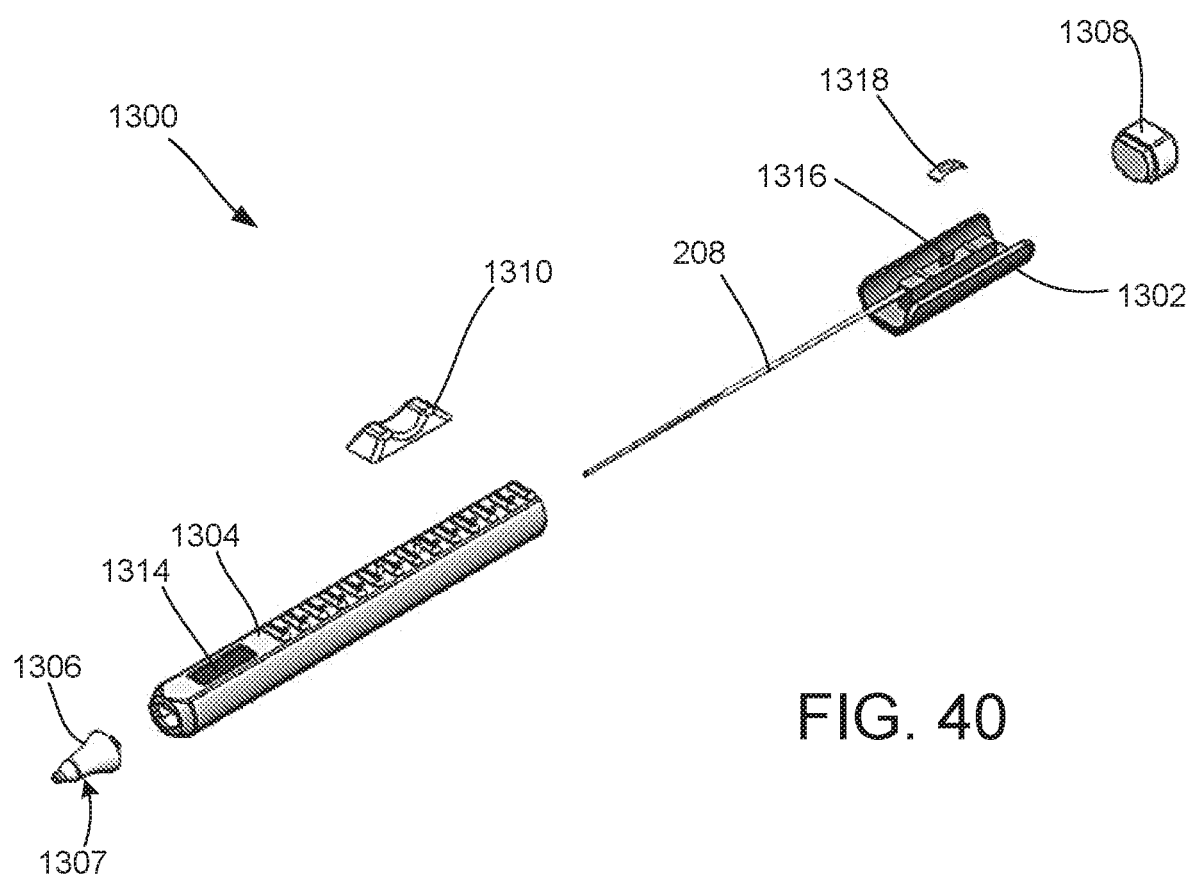
FIG. 40 is a perspective, exploded view of the medical device of FIG. 39.

FIG. 39 is a perspective view of another embodiment of a medical device 1300 consistent with the present disclosure. FIG. 40 is a perspective, exploded view of the medical device 1300. While medical device 1300 may share some similar in features as medical device 1000, the medical device 1300 is generally arranged in a different manner than those medical devices 1000, 1100, and 1200 previously described herein. For example, as shown, medical device 1300 includes a portion of a handle 1302 which includes a bone probe 208 fixed thereto, a depth gauge cylinder 1304, which generally forms most of the device 1300, slidably mounted over a portion of the handle 1302, specifically a handle body, and configured to slide along a length thereof, and a tip member 1306 releasably coupled to a distal end of the depth gauge cylinder 1304. The tip member 1306 may further include a radiopaque ring 1307 on a distal end.

The device 1300 further includes a display 1314 provided on the depth gauge cylinder 1304 configured to visually provide a digital readout of a depth measurement of a hole in bone. As illustrated, the depth gauge cylinder 1304 includes an elongate, hollow body which forms a majority of the device 1300, the portion of the handle 1302 is positioned along an underside of the depth gauge cylinder 1304. The device 1300 further includes a retaining cap 1308 for covering an open proximal end of the depth gauge cylinder 1304. The depth gauge cylinder 1304 further includes a repositionable thumb rest 1310 along a topside of the depth gauge cylinder 1304. The thumb rest 1310 may be repositioned at various positions along a length of the depth gauge cylinder 1304 via retaining tabs 1312.

Figure 41:
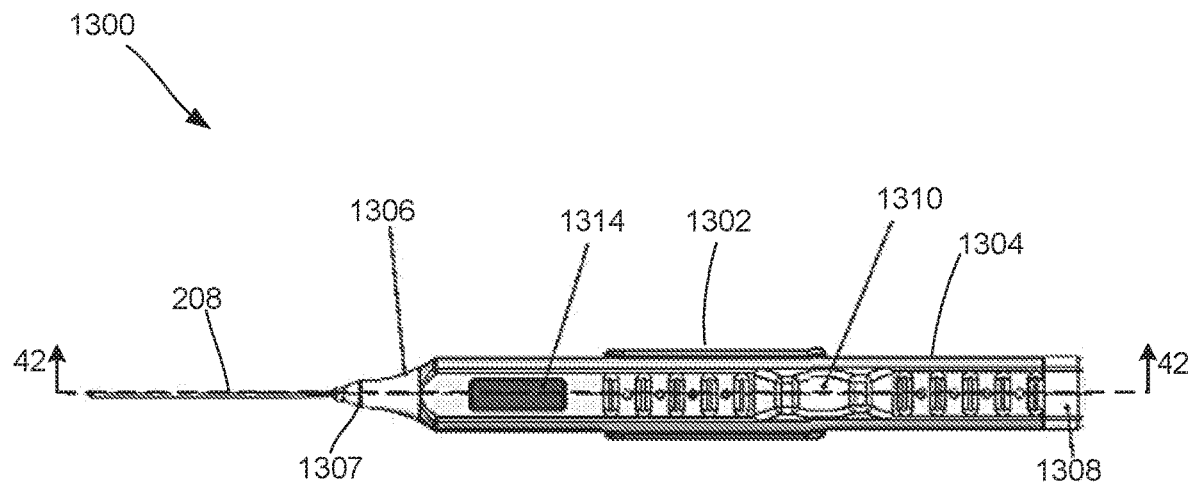
FIG. 41 is a top view of the medical device of FIG. 39 illustrating the depth gauge cylinder in the initial, default position relative to the handle and bone probe.
Figure 42:
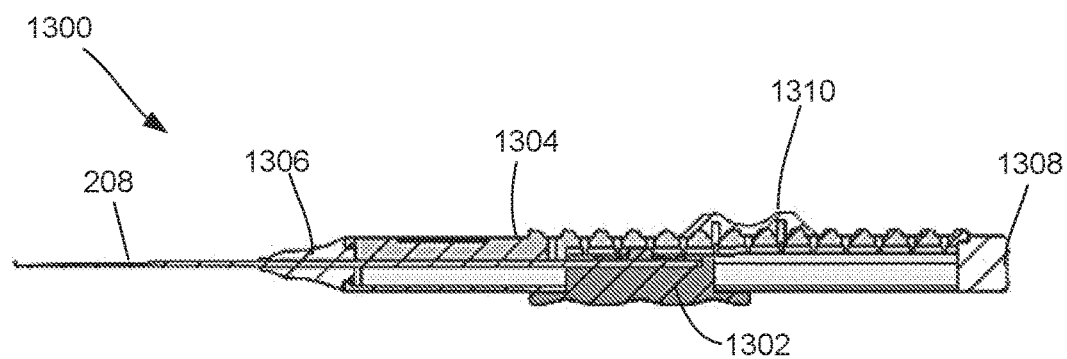
FIG. 42 is a cross-sectional view of the medical device taken along lines 42-42 of FIG. 41.
Figure 43:
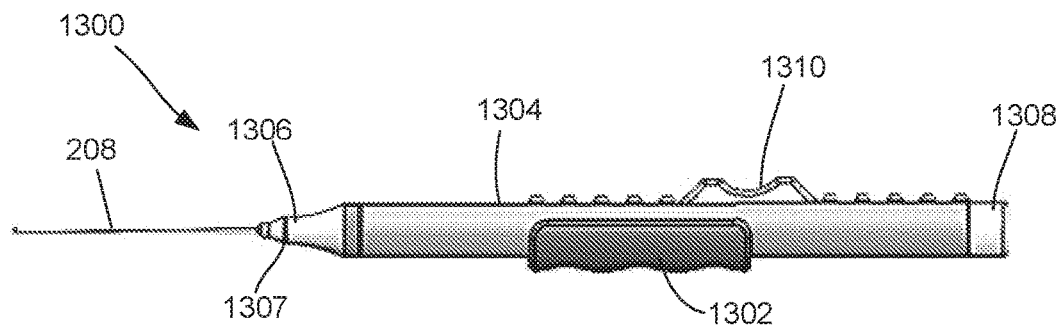
FIG. 43 is a side view of the medical device of FIG. 39.

FIG. 41 is a top view of the medical device 1300 illustrating the depth gauge cylinder 1304 in the initial, default position relative to the handle 1302 and bone probe 208. FIG. 42 is a cross-sectional view of the medical device taken along lines 42-42 of FIG. 41. FIG. 43 is a side view of the medical device 1300.

FIGS. 44A-44E illustrate a series of steps for performing a procedure of probing a fully drilled hole (i.e., a hole extending entirely through a bone for receipt of a bicortical bone screw) with a bone probe (similar to the bone probe of FIG. 4) and further establishing purchase of the probing tip of the bone probe with a side of the bone adjacent to the bicortical drilled hole to secure the bone probe in place and subsequently obtaining a depth measurement using one embodiment of a medical device, such as medical device 1000, consistent with the present disclosure.

As shown, the hole is drilled entirely through the bone (i.e., bicortical drill hole), and thus a surgeon will need to not only probe the interior surface of the hole, but further obtain an accurate measurement of the depth of the entire hole. Furthermore, a bone plate is positioned upon the bone which will require a tool to determine hole depth while accounting for a thickness of the bone plate.

Figures 44A, 44B, 44C:
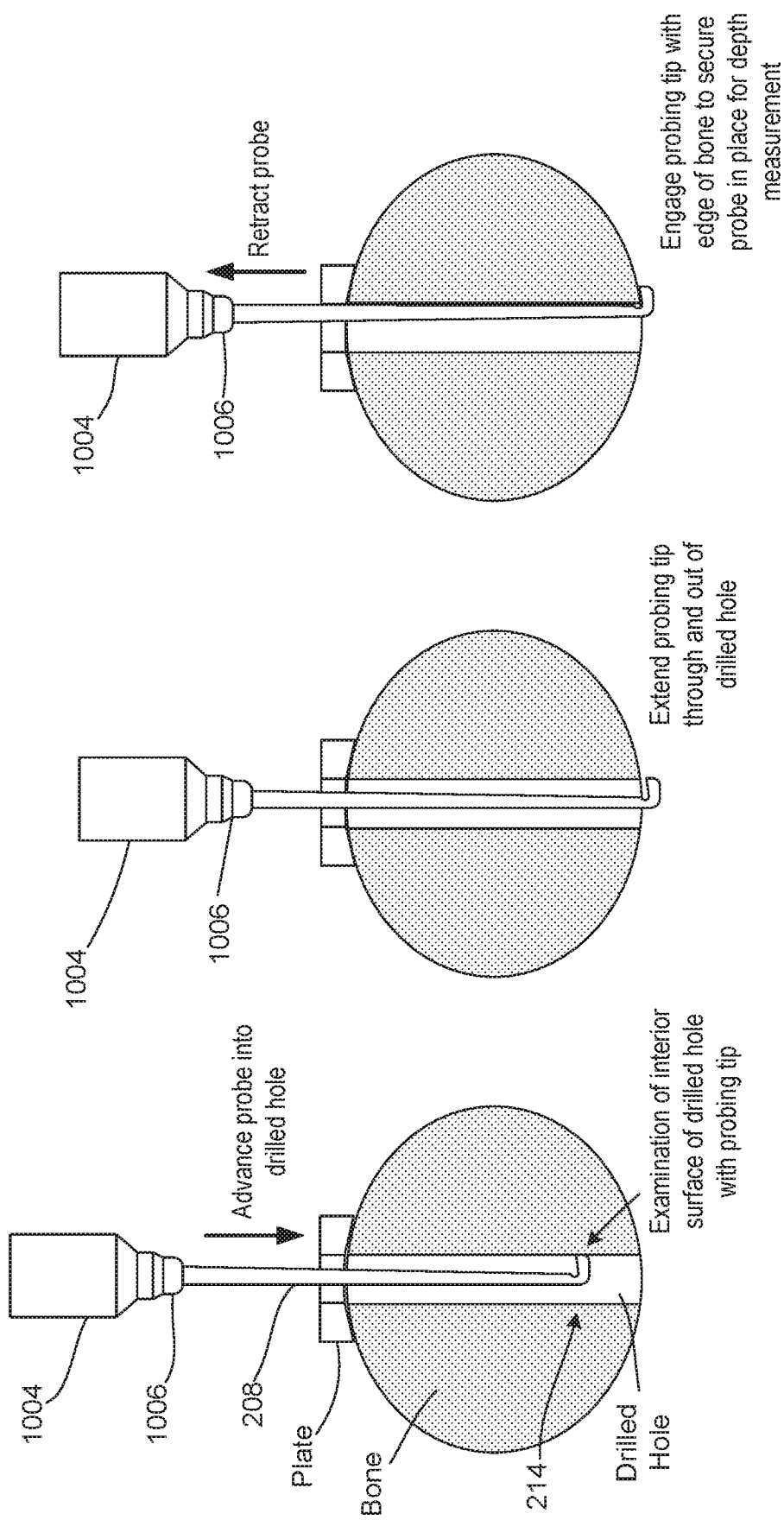
FIGS. 44A-44E illustrate a series of steps for performing a procedure of probing a fully drilled hole (i.e., a hole extending entirely through a bone for receipt of a bicortical bone screw) with a bone probe (similar to the bone probe of FIG. 4) and further establishing purchase of the probing tip of the bone probe with a side of the bone adjacent to the bicortical drilled hole to secure the bone probe in place and subsequently obtaining a depth measurement using the embodiment of a medical device consistent with the present disclosure.

As shown in FIG. 44A, a surgeon may first perform examination of the drilled hole with the probing tip 214 by advancing the bone probe 208 into the drilled hole. The surgeon may simply apply slight pressure such that a base portion of the probing tip contacts an interior surface of the hole and, in return, provides tactile feedback of the interior surface to the surgeon. The base portion is shaped so as to glide or easily slide along the interior surface, while still allowing sufficient contact to provide tactile feedback to the surgeon. The surgeon may then advance the probing tip 214 entirely through the hole, at which point, the base portion will cease contact with the interior surface and the surgeon will sense (via tactile feedback) that the end of the hole has been reached (shown in FIG. 44B).

At this point, upon the surgeon extending the probing tip 214 entirely through a bicortical drilled hole, the surgeon can then establish purchase between the top portion of the probing tip 214 and a portion of an opposing side of bone so as to secure the bone probe shaft 210 in place for subsequent depth measurements with the depth gauge cylinder 1004 and tip member 1006.

For example, as shown in FIG. 44C, the surgeon may simply position the substantially planar second side of the bone probe tip against the interior surface of the drilled hole and then retract (i.e., pull back) the probe shaft 210 such that the engagement surface of the top portion of the probing tip 214 comes into contact with a portion of the opposing side of the bone immediately adjacent to the opening of the hole. The engagement surface may be a substantially abrupt edge of the probing tip 214, in which the transition between the base portion and the top portion is sudden (e.g., sharp corner or edge). Accordingly, as the surgeon is pulling the bone probe shaft 210 back towards the hole, the engagement surface will begin to contact the bone. Upon securing the bone probe 208 in place, depth measurements may take place with the depth gauge cylinder 1004 and tip member 1006.

For example, with reference to medical device 1000, the bone probe 208 is generally fixed to the handle 1002 of the device 1000. The handle 1002 may include, for example, a proximal end including a grip portion to provide a surgeon with a means for applying a pulling force so as to draw the engagement surface of the probing tip of the bone probe into engagement with an exterior surface of bone immediately adjacent to a bicortical hole in the bone.

Figure 44E:
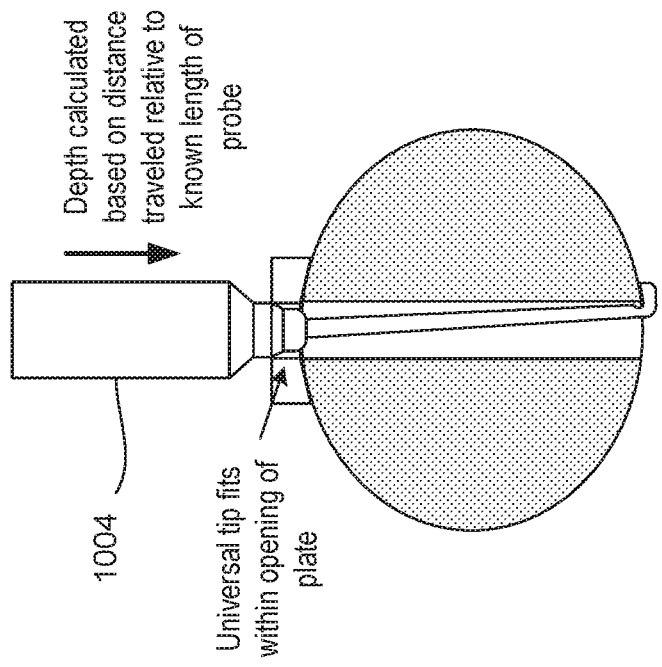
Figure 44D:
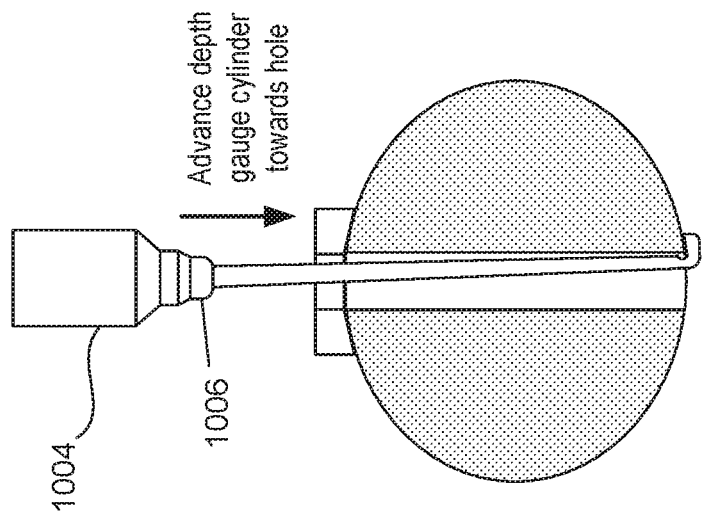

Accordingly, upon establishing purchase with an exterior surface of bone generally providing an edge of the exit point of the drilled (or otherwise pierced hole) via the probing tip, a surgeon need only continue pulling back on the handle to thereby maintain engagement of the bone probe with the exterior surface of bone and then slide the depth gauge cylinder 1004 in a direction towards the bone, as illustrated in FIG. 44D.

As illustrated in FIG. 44E, upon sliding the depth gauge cylinder 1004 towards the bone, at least a portion of the tip member 1006 will pass through an opening in the bone plate corresponding to the drilled hole until a portion of the stepped profile of the tip member 1006 makes contact with and engages a countersink portion of the opening in the bone plate. When the tip member 1006 is correctly positioned in the countersink of the bone plate, the most distal edge of the tip member 1006 will be aligned along the same plane as the bone-facing surface of the bone plate. For example, as previously described, the tip member 1006 includes a distal end including a profile corresponding to an opening in a bone plate through which a screw is to be received. More specifically, the tip member 1006 of the present disclosure is particularly useful in procedures in which a depth measurement is to be obtained with a bone plate in place (i.e., positioned where it would be mounted). As generally understood, it is preferable to countersink a screw when performing a bone implant fixation procedure so as to avoid any potential complications as a result of a screw head extending from a surface of bone or a bone plate. There are known generally geometries of a countersink in a bone plate hole (for receiving the screw), which include at least a mini, small, and large fragment, wherein the mini-frag is the most common. The profile of the distal end of the tip member 1006 comprises a stepped profile including multiple distinct and separate stepped portions, wherein each stepped portion has a different diameter (as illustrated in FIGS. 29A, 29B, and 29C) and tapers in diameter from a proximal position on the tip member towards a distal position of the tip member. Each of the separate stepped portions has a respective shape and/or diameter that corresponds to shapes and/or diameter of common countersink sizes provided in bone plates. Accordingly, the tip member 1006 may be considered universal in that the profile may allow for the tip member 1006 to fit most shapes, sizes, and geometries of screw sockets and bone plate openings with precision and accuracy. For example, the diameter at each stepped portion may correspond to a diameter of one of the typical geometries of the countersink (e.g., first diameter corresponds to large frag, second diameter corresponds to small frag, third diameter corresponds to mini-frag, etc.).

The sensor is then configured to generate an electronic signal based on the distance that the depth gauge cylinder 1004 traveled relative to the handle and bone probe, wherein the electronic signal is indicative of at least a depth of the hole. In particular, the sensor may include inductive or capacitive elements or assemblies configured to sense the location of a distal end of the depth gauge cylinder, for example, relative to a specific point along the handle, and, as a result, generate an electronic signal representing the distance there between as a result of movement (i.e., sliding) of the depth gauge cylinder. For example, the depth gauge cylinder may generally slide relative to the handle and bone probe between a most-proximal position and a most-distal position and a plurality of positions therebetween. As such, the depth gauge cylinder may be in the most-proximal position when in the default, initial position when depth measurement has not yet begun. Upon establishing engagement between the bone probe tip and the bone, the depth gauge cylinder may then be advanced in a direction towards the bone from the default, initial position until the tip member, specifically the stepped profile, makes contact with a countersink in the bone plate opening. The sensed distance traveled by the depth gauge cylinder is then used to calculate the depth of the hole. In particular, the device may include logic for determining hole depth based on known variables. For example, the length of the bone probe shaft extending from the distal end of the tip member when the depth gauge cylinder is in the initial, default position (i.e., the most-proximal position relative to the handle) may be known and programmed into the logic. As such, the sensed distance traveled by the depth gauge cylinder from the initial, default position until the tip member, specifically the stepped profile, makes contact with a countersink in the bone plate opening, may simply be subtracted from the known length of the bone probe shaft to thereby provide the depth of the hole.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A device for examination and measurement of a hole formed through a bone, the device comprising:
   a handle;
   a bone probe fixed to the handle and extending from a distal end thereof, the bone probe comprising a shaft including a distal end defining a probing tip comprising a portion including at least an engagement surface shaped and configured to establish purchase with an exterior surface of bone adjacent to a hole upon sufficient application of force to the shaft;
   a depth gauge cylinder slidably mounted to a portion of the handle, the depth gauge cylinder comprising a hollow body including a lumen in which at least a portion of the handle and the bone probe shaft are received within, wherein the depth gauge cylinder is operable to slide along a length of the handle relative to a longitudinal axis of the handle;
   a tip member releasably coupled to a distal end of the depth gauge cylinder and operable to correspondingly slide with the depth gauge cylinder, the tip member comprising an opening through which at least the bone probe shaft is received, the tip member further comprising a distal end including a profile corresponding to an opening in a bone plate through which a screw is to be received; and
   a sensor configured to generate an electronic signal indicative of a depth of the hole, wherein the electronic signal varies in relation to distance traveled by the depth gauge cylinder relative to the handle and bone probe.

2. The device of claim 1, wherein the depth gauge cylinder is slidable along a length of the handle between a most-proximal position and a most-distal position and a plurality of positions therebetween.

3. The device of claim 2, wherein the sensor is configured to sense a first position and a second position of the depth gauge cylinder along the length of handle.

4. The device of claim 3, wherein the electronic signal is based on a measurement of distance between the first position and the second position of the depth gauge cylinder along the length of handle.

5. The device of claim 4, wherein the sensor is in electronic communication with a printed circuit board.

6. The device of claim 5, wherein the handle and the depth gauge cylinder are retained to one another by way of a member to thereby prevent the depth gauge cylinder from disengaging with the handle.

7. The device of claim 4, wherein the portion of handle received by the depth gauge cylinder comprises a cylindrical body.

8. The device of claim 4, wherein the handle comprises a rigid material.

9. The device of claim 4, wherein the tip member comprises a universal distal end configured to fit a variety of bone plates.

10. The device of claim 9, wherein the profile of the universal distal end comprises a stepped profile including at least two or more distinct and separate stepped portions, wherein each stepped portion including a different diameter.

11. The device of claim 10, wherein the diameters of the at least two or more stepped portions decrease from a most proximal stepped portion to a most distal stepped portion.

12. The device of claim 11, wherein the universal tip comprises sloped surfaces between the stepped portions.

13. The device of claim 12, further comprising a display on the handle configured to visually provide a digital readout of a depth measurement of the hole based on the electronic signal from the sensor.

14. The device of claim 12, further comprising a display on the depth gauge cylinder configured to visually provide a digital readout of a depth measurement of the hole based on the electronic signal from the sensor.

15. The device of claim 12, further comprising a wireless transmitter/receiver configured to wirelessly communicate and exchange information, including the electronic signal, with a wireless display or computing device for at least visually providing a depth measurement of the hole based on the electronic signal from the sensor.

* * * * *